(12) United States Patent
Taniguchi

(10) Patent No.: US 11,969,295 B2
(45) Date of Patent: Apr. 30, 2024

(54) TECHNIQUES TO PREVENT AN OCCURRENCE OF AN ARTIFACT DUE TO RESIDUAL ECHOES IN AN ULTRASOUND DIAGNOSTIC DEVICE

(71) Applicant: Konica Minolta, Inc., Tokyo (JP)

(72) Inventor: Tetsuya Taniguchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 141 days.

(21) Appl. No.: 17/371,244

(22) Filed: Jul. 9, 2021

(65) Prior Publication Data
US 2022/0015743 A1    Jan. 20, 2022

(30) Foreign Application Priority Data

Jul. 16, 2020 (JP) ................. 2020-122387

(51) Int. Cl.
*A61B 8/08* (2006.01)
*A61B 8/00* (2006.01)
*A61B 8/14* (2006.01)

(52) U.S. Cl.
CPC .............. *A61B 8/5276* (2013.01); *A61B 8/14* (2013.01); *A61B 8/4461* (2013.01); *A61B 8/4477* (2013.01)

(58) Field of Classification Search
CPC ............ G01S 15/8963; G01S 7/52077; G01S 7/52085; G01S 7/52038
See application file for complete search history.

(56) References Cited

U.S. PATENT DOCUMENTS 5,617,863 A * 4/1997 Roundhill ........... G01S 7/52085
                                                    600/447
5,706,819 A * 1/1998 Hwang ............... G01S 7/52038
                                                    600/458

(Continued)

FOREIGN PATENT DOCUMENTS

JP    2003512914 A    4/2003
JP    2003299653 A    10/2003

(Continued)

OTHER PUBLICATIONS

Japanese Patent Office, "Notice of Reasons for Refusal", dated Feb. 20, 2024 for the related Japanese patent application No. 2020-122387 and its full English translation, 14 pages.

*Primary Examiner* — Joel Lamprecht
*Assistant Examiner* — Nyrobi Celestine
(74) *Attorney, Agent, or Firm* — Lucas & Mercanti, LLP

(57) ABSTRACT

An ultrasound diagnostic device includes a transmitter that causes an ultrasound probe including a plurality of transducers aligned in an azimuth direction to perform a plurality of set transmissions including a plurality of types of ultrasound transmissions for a transmission line which is common, while changing a position of the transmission line in the azimuth direction, a receiver that acquires, from the ultrasound probe, received signals based on reflected waves for the plurality of types of ultrasound transmissions and generates a plurality of types of acoustic line signals, and a hardware processor that generates an imaging signal based on the plurality of types of acoustic line signals. During a time interval between the plurality of types of the ultrasound transmissions in a first set transmission, the transmitter performs at least one of the plurality of types of ultrasound transmissions in a second set transmission.

15 Claims, 31 Drawing Sheets

| TRANSMISSION ORDER (L) | SCAN LINE NUMBER (i) | TRANSMIT WAVE TYPE (q) |
|---|---|---|
| 1 | 1 | Tx1₁ |
| 2 | 97 | Tx1₉₇ |
| 3 | 1 | Tx2₁ |
| 4 | 97 | Tx2₉₇ |
| 5 | 2 | Tx1₂ |
| 6 | 98 | Tx1₉₈ |
| 7 | 2 | Tx2₂ |
| 8 | 98 | Tx2₉₈ |
| ⋮ | ⋮ | ⋮ |
| 382 | 96 | Tx1₉₆ |
| 383 | 192 | Tx1₁₉₂ |
| 384 | 96 | Tx2₉₆ |
| 385 | 192 | Tx2₁₉₂ |

(56) References Cited

U.S. PATENT DOCUMENTS

| | | | | |
|---|---|---|---|---|
| 5,980,459 A * | 11/1999 | Chiao | | A61B 8/06 600/458 |
| 6,159,153 A * | 12/2000 | Dubberstein | | G01S 15/8915 600/443 |
| 6,171,246 B1 * | 1/2001 | Averkiou | | G01S 15/8981 600/458 |
| 6,186,950 B1 * | 2/2001 | Averkiou | | A61B 8/13 600/443 |
| 6,193,662 B1 * | 2/2001 | Hwang | | G01S 7/52095 600/458 |
| 6,440,074 B1 * | 8/2002 | Averkiou | | G01S 15/8952 600/443 |
| 6,620,103 B1 * | 9/2003 | Bruce | | G01S 7/52085 600/458 |
| 6,682,482 B1 * | 1/2004 | Krishnan | | G01S 7/52039 600/443 |
| 2003/0229285 A1 * | 12/2003 | Simpson | | A61B 8/481 600/458 |
| 2004/0087857 A1 * | 5/2004 | Napolitano | | G01S 7/52046 600/443 |
| 2004/0102702 A1 * | 5/2004 | Shimazaki | | G01S 7/52095 600/447 |
| 2005/0148875 A1 * | 7/2005 | Sato | | A61B 8/06 600/453 |
| 2005/0154305 A1 * | 7/2005 | Kamiyama | | G01S 7/52085 600/443 |
| 2009/0118617 A1 * | 5/2009 | Azuma | | G01S 15/8995 600/447 |
| 2015/0087985 A1 * | 3/2015 | Yoshiara | | G01S 7/52046 600/443 |
| 2015/0141830 A1 * | 5/2015 | Kakee | | A61B 8/5269 600/447 |
| 2016/0296203 A1 * | 10/2016 | Konofagou | | A61B 8/14 |
| 2018/0000458 A1 * | 1/2018 | Park | | G01S 15/8915 |
| 2019/0015074 A1 * | 1/2019 | Gu | | A61B 8/5223 |
| 2019/0282212 A1 * | 9/2019 | Rosenzweig | | A61B 8/5269 |
| 2019/0353764 A1 * | 11/2019 | Vignon | | G01S 7/52046 |
| 2020/0158843 A1 * | 5/2020 | Schmied | | A61B 8/483 |
| 2021/0085293 A1 * | 3/2021 | Gong | | G01S 15/8915 |
| 2021/0353251 A1 * | 11/2021 | Hope Simpson | | A61B 8/14 |

FOREIGN PATENT DOCUMENTS

| | | | | |
|---|---|---|---|---|
| JP | 2004-181209 A | | 7/2004 | |
| JP | 2007-244501 A | | 9/2007 | |
| JP | 2007244501 A | * | 9/2007 | ............... A61B 8/14 |
| JP | 2010-017373 A | | 1/2010 | |
| WO | WO-2015198824 A1 | * | 12/2015 | ............... A61B 8/14 |
| WO | 2019/181597 A1 | | 9/2019 | |

* cited by examiner

| TRANSMISSION ORDER (L) | SCAN LINE NUMBER (i) | TRANSMIT WAVE TYPE (q) |
|---|---|---|
| 1 | 1 | $Tx1_1$ |
| 2 | 97 | $Tx1_{97}$ |
| 3 | 1 | $Tx2_1$ |
| 4 | 97 | $Tx2_{97}$ |
| 5 | 2 | $Tx1_2$ |
| 6 | 98 | $Tx1_{98}$ |
| 7 | 2 | $Tx2_2$ |
| 8 | 98 | $Tx2_{98}$ |
| ⋮ | ⋮ | ⋮ |
| 382 | 96 | $Tx1_{96}$ |
| 383 | 192 | $Tx1_{192}$ |
| 384 | 96 | $Tx2_{96}$ |
| 385 | 192 | $Tx2_{192}$ |

FIG. 5

| AREA | TRANSMISSION ORDER (L) | SCAN LINE NUMBER (i) | TRANSMIT WAVE TYPE (q) |
|---|---|---|---|
| 1/2 | 1 | 1 | $Tx1_1$ |
| | 2 | 49 | $Tx1_{49}$ |
| | 3 | 1 | $Tx2_1$ |
| | 4 | 49 | $Tx2_{49}$ |
| | ⋮ | ⋮ | ⋮ |
| | 193 | 48 | $Tx1_{48}$ |
| | 194 | 96 | $Tx1_{96}$ |
| | 195 | 48 | $Tx2_{48}$ |
| | 196 | 96 | $Tx2_{96}$ |
| 2/2 | 197 | 135 | $Tx1_{135}$ |
| | 198 | 97 | $Tx1_{97}$ |
| | 199 | 135 | $Tx2_{135}$ |
| | 200 | 97 | $Tx2_{97}$ |
| | ⋮ | ⋮ | ⋮ |
| | 382 | 192 | $Tx1_{192}$ |
| | 383 | 134 | $Tx1_{134}$ |
| | 384 | 192 | $Tx2_{192}$ |
| | 385 | 134 | $Tx2_{134}$ |

FIG. 14

| TRANSMISSION ORDER (L) | SCAN LINE NUMBER (i) | TRANSMIT WAVE TYPE (q) |
|---|---|---|
| 1 } T1 | 1 | $Tx1_1$ ⊕ |
| 2 } T2 | 1 | $Tx2_1$ |
| 3 } T1 | 2 | $Tx1_2$ ⊕ |
| 4 | 2 | $Tx2_2$ |
| ⋮ | ⋮ | ⋮ |
| 194 } T1 | 97 | $Tx1_{97}$ ⊕ |
| 195 } T2 | 97 | $Tx2_{97}$ |
| 196 } T1 | 98 | $Tx1_{98}$ ⊕ |
| 197 } T2 | 98 | $Tx2_{98}$ |
| 198 } T1 | 99 | $Tx1_{99}$ ⊕ |
| 199 | 99 | $Tx2_{99}$ |
| ⋮ | ⋮ | ⋮ |
| 382 } T1 | 191 | $Tx1_{191}$ ⊕ |
| 383 } T2 | 191 | $Tx2_{191}$ |
| 384 } T1 | 192 | $Tx1_{192}$ ⊕ |
| 385 | 192 | $Tx2_{192}$ |

| TRANSMISSION ORDER (L) | SCAN LINE NUMBER (i) | TRANSMIT WAVE TYPE (q) |
|---|---|---|
| 1 | 1 | $Tx1_1$ |
| 2 | 1 | $Tx2_1$ |
| 3 | 2 | $Tx1_2$ |
| 4 | 2 | $Tx2_2$ |
| ⋮ | ⋮ | ⋮ |
| 194 | 97 | $Tx1_{97}$ |
| 195 | 97 | $Tx2_{97}$ |
| 196 | 98 | $Tx1_{98}$ |
| 197 | 98 | $Tx2_{98}$ |
| 198 | 99 | $Tx1_{99}$ |
| 199 | 99 | $Tx2_{99}$ |
| ⋮ | ⋮ | ⋮ |
| 382 | 191 | $Tx1_{191}$ |
| 383 | 191 | $Tx2_{191}$ |
| 384 | 192 | $Tx1_{192}$ |
| 385 | 192 | $Tx2_{192}$ |

| TRANSMISSION ORDER (L) | SCAN LINE NUMBER (i) | TRANSMIT WAVE TYPE (q) |
|---|---|---|
| 1 } T1 | 1 | $Tx1_1$ |
| 2 } T2 | 1 | $Tx2_1$ |
| 3 } T1 | 2 | $Tx2_2$ |
| 4 | 2 | $Tx1_2$ |
| ⋮ | ⋮ | ⋮ |
| 194 } T1 | 97 | $Tx1_{97}$ |
| 195 } T2 | 97 | $Tx2_{97}$ |
| 196 } T1 | 98 | $Tx2_{98}$ |
| 197 } T2 | 98 | $Tx1_{98}$ |
| 198 } T1 | 99 | $Tx1_{99}$ |
| 199 | 99 | $Tx2_{99}$ |
| ⋮ | ⋮ | ⋮ |
| 382 } T1 | 191 | $Tx1_{191}$ |
| 383 } T2 | 191 | $Tx2_{191}$ |
| 384 } T1 | 192 | $Tx2_{192}$ |
| 385 | 192 | $Tx1_{192}$ |

TECHNIQUES TO PREVENT AN OCCURRENCE OF AN ARTIFACT DUE TO RESIDUAL ECHOES IN AN ULTRASOUND DIAGNOSTIC DEVICE

CROSS REFERENCE TO RELATED APPLICATIONS

The entire disclosure of Japanese Patent Application No. 2020-122387 filed on Jul. 16, 2020 is incorporated herein by reference in its entirety.

BACKGROUND

Technological Field

The present invention relates to an ultrasound diagnostic device and a non-transitory computer readable storage medium and, in particular, to a beamforming method for transmission and reception in an ultrasound diagnostic device.

Description of Related Art

An ultrasound diagnostic device is a medical imaging device that acquires in vivo information by using an ultrasonic pulse-reflection technique and displays the in vivo information in the form of a cross-sectional image. The ultrasound diagnostic device transmits ultrasound into the inside of a subject with an ultrasound probe (hereinafter simply referred to as "probe"), receives reflected ultrasound (echo) generated by the difference in the acoustic impedance between the subject's tissues, generates an ultrasound cross-sectional image depicting the structure of the subject's internal tissues on the basis of electrical signals obtained through the reception, and displays the cross-sectional image on a monitor (hereinafter referred to as a "display unit"). For ultrasound diagnostic devices, a variety of approaches have been developed to improve the real-time performance in displaying a moving image, and a variety of techniques have been proposed for reducing an artifact due to residual echo that occurs when the pulse repetition cycle is decreased (refer to Japanese Patent Application Laid-Open No. 2004-181209, Japanese Patent Application Laid-Open No. 2007-244501, and Japanese Patent Application Laid-Open No. 2010-17373).

SUMMARY

However, in recent years, as the demand for high real-time performance in moving image rendering has increased and the pulse repetition period has been decreased to improve the real-time performance, an artifact caused by residual echoes from a highly reflective tissue located deeper than the imaging region has often become a problem.

Accordingly, the present invention provides an ultrasound diagnostic device and a non-transitory computer readable storage medium that ensure the real-time performance during displaying a moving image and reduces the occurrence of an artifact caused by residual echoes from highly reflective tissue located deeper than the imaging region.

To achieve at least one of the abovementioned objects, according to an aspect of the present invention, an ultrasound diagnostic device reflecting one aspect of the present invention comprises a transmitter that causes an ultrasound probe including a plurality of transducers aligned in an azimuth direction to perform a plurality of set transmissions including a plurality of types of ultrasound transmissions for a transmission line which is common, while changing a position of the transmission line in the azimuth direction, a receiver that acquires, from the ultrasound probe, received signals based on reflected waves for the plurality of types of ultrasound transmissions and generates a plurality of types of acoustic line signals, and a hardware processor that generates an imaging signal based on the plurality of types of acoustic line signals. During a time interval between the plurality of types of the ultrasound transmissions in a first set transmission, the transmitter performs at least one of the plurality of types of ultrasound transmissions in a second set transmission that differs from the first set transmission.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 5 is a diagram illustrating the transmission sequence at the transmitter;

FIG. 14 illustrates an example of a transmission sequence at the transmitter of the ultrasound diagnostic device according to a first modification of the first embodiment;

FIG. 16 illustrates the transmission sequence at the transmitter of the ultrasound diagnostic device according to a second embodiment;

FIG. 20 illustrates the transmission sequence at the transmitter of the ultrasound diagnostic device according to the third embodiment;

FIG. 25 illustrates the transmission sequence at the transmitter of the ultrasound diagnostic device according to a third modification;

DETAILED DESCRIPTION OF EMBODIMENTS

Hereinafter, one or more embodiments of the present invention will be described with reference to the drawings. However, the scope of the invention is not limited to the disclosed embodiments.

Background to Embodiments of Invention

In recent years, in displaying a moving image by an ultrasound diagnostic device, an artifact due to residual echoes from a highly reflective tissue located deeper than the imaging region has often become a problem.

Figure 30A:
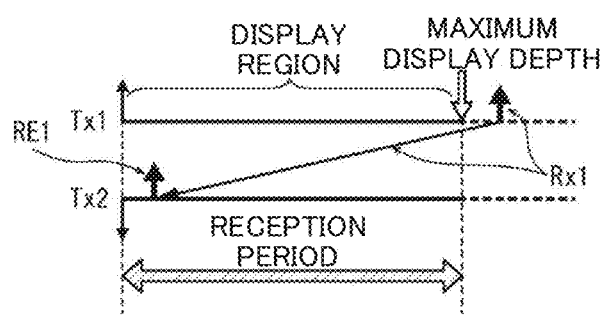
FIG. 30A is a schematic illustration of the way the reflected wave based on an ultrasound beam transmitted by an existing ultrasound diagnostic device reaches a transducer.
Figure 30B:
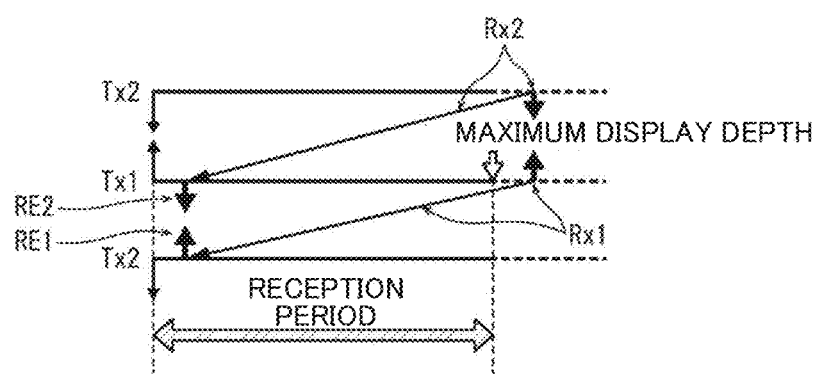
FIG. 30B is a schematic illustration of the way the reflected wave based on an ultrasound beam transmitted by an existing ultrasound diagnostic device reaches a transducer.
Figure 31:
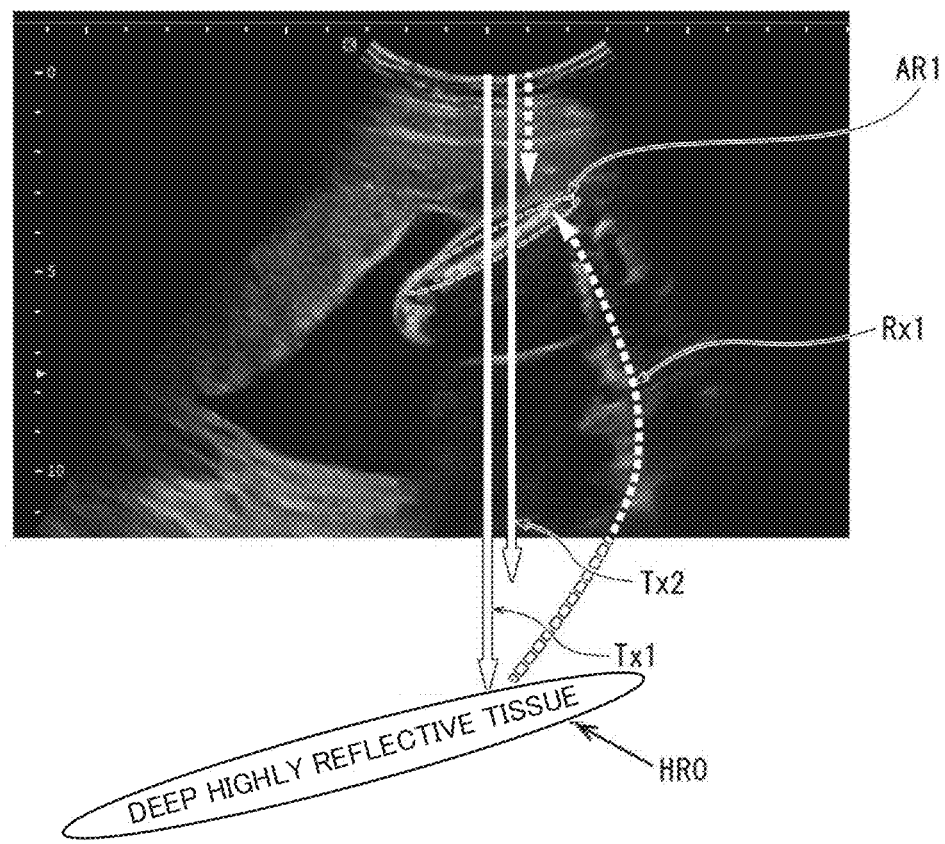
FIG. 31 is a schematic illustration of the propagation paths of the transmit wave and the reflected wave in the cross section of the subject during transmission performed by an existing ultrasound diagnostic device.

FIGS. 30A and 30B are schematic illustrations of the way a reflected wave based on a transmitted ultrasound beam reaches a transducer in an existing ultrasound diagnostic device. FIG. 31 is a schematic illustration of the propagation paths of the transmit wave and reflected wave in the cross section of a subject in an existing ultrasound diagnostic device.

More specifically, FIGS. 30A and 30B are schematic illustrations of transmission and reception regarding a pair of transmit waves Tx1 and Tx2 with different polarities on the same scan line using the Pulse Inversion (PI) method in Tissue Harmonic Imaging (THI) for imaging harmonic components. The abscissa represents the depth corresponding to the display region for the transmit waves Tx1 and Tx2, and the direction on the ordinate represents the polarity of each of the transmit and reflected waves.

For each of the transmit waves Tx1 and Tx2, imaging is performed on the subject tissue at a depth corresponding to the display region up to the maximum display depth on the basis of the reflected waves received during the reception period.

In the example illustrated in FIG. 30A, when transmission and reception of the transmit wave Tx2 are started immediately after reception of the transmit wave Tx1 for the display region is performed, the reflected wave Rx1 of the transmit wave Tx1 reflected by highly reflective tissue located at a depth deeper than the maximum display depth arrives at the transducer within the reception period of transmit wave Tx2 for the same scan line. Thus, the reflected wave Rx1 is coupled in during reception for the transmit wave Tx2 and is detected as residual echo RE1. In this case, as illustrated in FIG. 31, the residual echo RE1 based on the reflected wave Rx1 from a highly reflective tissue HRO located deeper than the display region is displayed in the display region as artifact AR1.

Furthermore, in the example illustrated in FIG. 30B, a reflected wave Rx2 from a deep highly reflective tissue based on the immediately preceding transmit wave Tx2 for an adjacent scan line reaches the transducer within the reception period of the transmit wave Tx1 for the current scan line. Thus, the reflected wave Rx2 is coupled in during reception for the transmit wave Tx1 and is detected as residual echo RE2, in addition to the residual echo RE1 of the transmit wave Tx1. Even in this case, the residual echo RE2 based on the reflected wave Rx2 from the deep highly reflective tissue HRO is displayed in the display region as an artifact.

To solve the problem, as mentioned above, techniques have been proposed to prevent the occurrence of an artifact caused by residual echoes in ultrasound diagnostic devices.

For example, Japanese Patent Application Laid-Open No. 2004-181209 describes a technique in which a dummy transmission-reception period is added to the pair of transmit/receive events in the pulse inversion method to cancel out residual echoes between the pair of transmit/receive events and the dummy transmission-reception, or a dummy reception period is provided to cancel out residual echoes between the pair of transmit/receive events and the dummy reception.

As another technique, Japanese Patent Application Laid-Open No. 2007-244501 describes a technique for generating a plurality of images by transmission and reception of ultrasound waves having different multiple pulse repetition frequencies, providing a virtual image determination unit to determine the occurrence of an artifact due to residual multiple echoes on the basis of the generated multiple image data, and reducing the pulse repetition frequency if an artifact occurs.

As still another technique, Japanese Patent Application Laid-Open No. 2010-17373 describes a technique in which Doppler reception data and a correction echo are acquired in a plurality of azimuthal directions by transmitting and receiving ultrasound a plurality of times at unequal intervals in the same azimuth direction and changing the azimuth direction in which the ultrasound is transmitted and received, Doppler reception data with residual echo removed or reduced are acquired by correcting the Doppler reception data using the correction echo, and blood flow information is obtained from the Doppler reception data with residual echo removed or reduced.

However, the technique described in Japanese Patent Application Laid-Open No. 2004-181209 requires additional processing time corresponding to the third transmission-reception or the third reception for a pair of transmit/receive events according to the pulse inversion method and, thus, the frame rate is not improved.

In addition, the technique described in Japanese Patent Application Laid-Open No. 2007-244501 assumes that there is no movement between frames of the image and, thus, it is difficult to make an accurate determination during a probe operation.

Furthermore, although the technique described in Japanese Patent Application Laid-Open No. 2010-17373 is effective for Doppler transmission and reception that requires a large number of transmit/receive events, the method is not effective for the pulse inversion method, which consists of a pair of transmit/receive events.

In recent years, there has been an increasing demand for high real-time performance of moving image rendering performed by an ultrasound diagnostic device that displays a B-mode image using spatial compounding, a moving image in a color Doppler mode, or a moving image to observe the heart of a fetus. However, when the pulse repetition period is decreased to improve the real-time performance, the problem of an artifact caused by residual echo from a highly reflective tissue located deeper than the imaging region become prominent and, thus, further improvement of the artifact caused by residual echo is required.

Accordingly, the present inventor has intensively studied the configuration of a low-cost ultrasound diagnostic device that does not require complicated transmission control to prevent the occurrence of an artifact due to residual echoes from a highly reflective tissue located deeper than the imaging region, without degrading the real-time performance during displaying a moving image. As a result, the present inventor has conceived of an idea of an ultrasound diagnostic device, an ultrasound signal processing method, and a non-transitory computer readable storage medium according to the present disclosure.

First Embodiment

Overview

The ultrasound signal processing method according to the first embodiment is a method for generating an image by using multiple-rate transmission, in which only a first transmit-receive event (transmission and reception using transmit wave Tx1) is performed a plurality of times in multiple spatially different regions and, thereafter, a second transmit-receive event (transmission and reception using transmit wave Tx2) is sequentially performed at the scan line position the same as that in the first transmit-receive event, and the results are used for reception calculation.

By setting multiple regions spatially apart from one another such that residual echo from another region is not received and performing transmission and reception, coupling of residual echo from scanning of adjacent scan lines can be prevented. In addition, in the case of two-region division (Tx1-Tx1-Tx2-Tx2- . . . ), the actual transmission interval between transmission and reception of transmit wave Tx1 and transmission and reception of transmit wave Tx2 for the same scan line can be doubled. In the case of three-region division (Tx1-Tx1-Tx1-Tx2-Tx2-Tx2- . . . ), the actual transmission interval can be tripled. Thus, coupling of residual echo from the transmit wave Tx1 into transmit wave Tx2 can be significantly reduced at short actual transmission intervals without sacrificing the frame rate.

Configuration

Ultrasound diagnostic device 100 according to the first embodiment is described below with reference to the accompanying drawings.

Configuration of Ultrasound Diagnostic System

Figure 1:
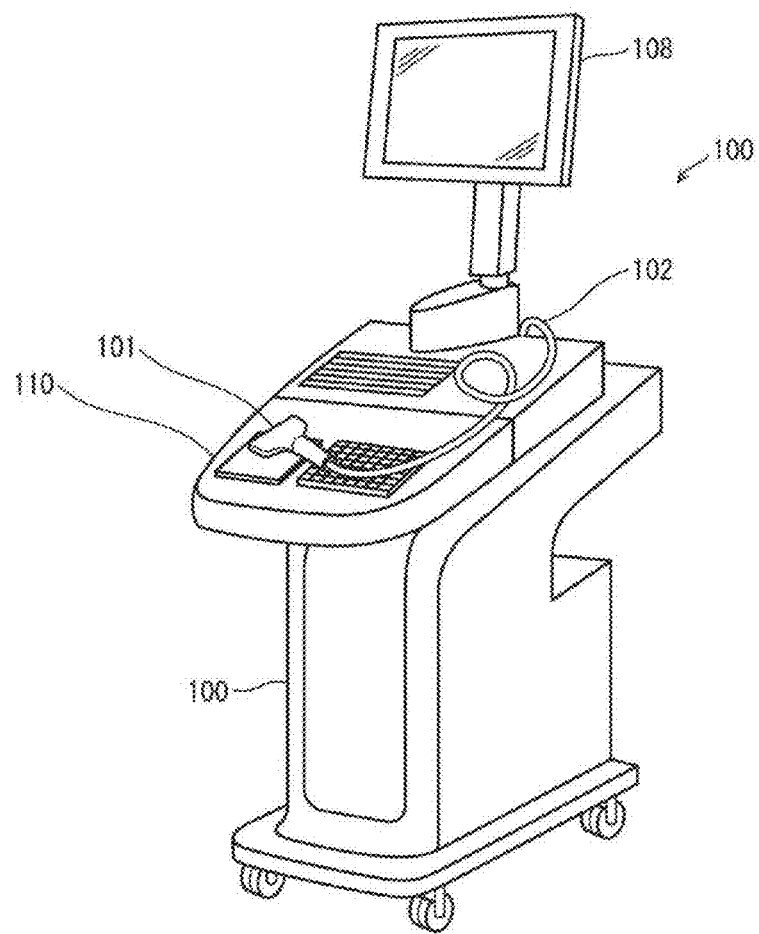
FIG. 1 is an external view of an ultrasound diagnostic system including an ultrasound diagnostic device according to the first embodiment.
Figure 2:
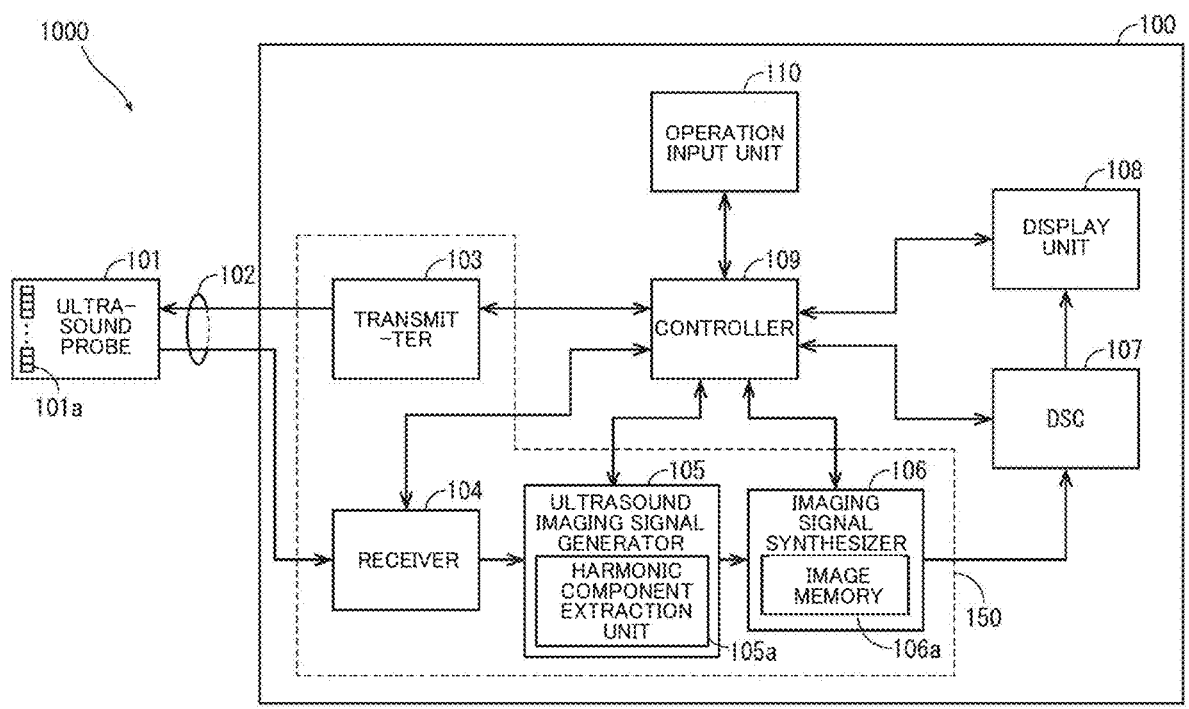
FIG. 2 is a functional block diagram illustrating the configuration of the ultrasound diagnostic device.

FIG. 1 is an external view of an ultrasound diagnostic system 1000 including ultrasound diagnostic device 100 according to the first embodiment. FIG. 2 is a functional block diagram illustrating the configuration of ultrasound diagnostic device 100. As illustrated in FIG. 1, ultrasound diagnostic system 1000 includes probe 101 having a plurality of transducers 101a lined up on the surface of the tip each transmitting ultrasound toward a subject and receives a reflected wave of the transmit wave, ultrasound diagnostic device 100 that causes probe 101 to transmit and receive ultrasound and generates an ultrasound image on the basis of signals output from probe 101, a display unit 108 that displays the ultrasound image on a screen, and operation input unit 110 that receives the operation input from an operator. Probe 101 is configured to be connected to ultrasound diagnostic device 100 by cable 102. Note that probe 101 may be included in ultrasound diagnostic device 100, and display unit 108 may not be included in ultrasound diagnostic device 100.

Overview of Configuration of Ultrasound Diagnostic Device

Ultrasound diagnostic device 100 includes transmitter 103 and receiver 104. Transmitter 103 selects, from among transducers 101a of probe 101, the transducers used during transmission or reception and controls the point in time to apply a high voltage to the selected transducers 101a of probe 101 for transmitting ultrasound via a multiplexer (not illustrated) that ensures input from and output to the selected transducers. Receiver 104 amplifies electrical signals obtained from a plurality of transducers 101a on the basis of a reflected wave of ultrasound received by probe 101, A/D-converts the electrical signals, and performs receive beamforming to generate acoustic line signals (DAS data: Delay and Sum Data). Ultrasound diagnostic device 100 further includes harmonic component extraction unit 105a that extracts the harmonic components from an acoustic line signal, which is an output signal from receiver 104, and ultrasound imaging signal generator 105 that performs processing, such as envelope detection and logarithmic compression, on the acoustic line signal and its harmonic components to convert them into the luminance and, thereafter, transforms the luminance signals into coordinates in the Cartesian coordinate system to generate an ultrasound image (a B-mode image). Hereinafter, ultrasound imaging signal generator 105 is referred to as imaging signal generator 105. Ultrasound diagnostic device 100 further includes imaging signal synthesizer 106 including image memory 106a. Imaging signal synthesizer 106 synthesizes subframe data and the like of an ultrasound image to synthesize an ultrasound imaging signal. Ultrasound diagnostic device 100 further includes DSC 107 that outputs the frame data of the ultrasound image to display unit 108, display unit 108, and controller 109 that controls the constituent elements. Ultrasound diagnostic device 100 may further include a data storage (not illustrated) that stores the acoustic line signals output from receiver 104 and the ultrasound imaging signals output from ultrasound imaging signal generator 105.

Of these constituent elements, transmitter 103, receiver 104, imaging signal generator 105, and imaging signal synthesizer 106 constitute ultrasound signal processing device 150.

Each of the elements that constitute ultrasound diagnostic device 100, such as transmitter 103, receiver 104, imaging signal generator 105, imaging signal synthesizer 106, DSC 107, and controller 109, is achieved by a hardware circuit, such as an FPGA (Field Programmable Gate Array), an ASIC (Application Specific Integrated Circuit), or the like. Alternatively, the elements may be achieved by a programmable device, such as a CPU (Central Processing Unit), a GPGPU (General-Purpose computing on Graphics Processing Unit), or processor, and software. Each of the constituent elements can be a single circuit component or an aggregate of a plurality of circuit components. Still alternatively, the plurality of constituent elements can be combined to form a single circuit component or an aggregate of a plurality of circuit components.

Image memory 106a and the data storage are computer-readable storage media, which can be, for example, a flexible disk, a hard disk, an MO, a DVD, a DVD-RAM, or a semiconductor memory. Note that image memory 106a and the data storage may be a storage device externally connected to ultrasound diagnostic device 100.

The configuration of ultrasound diagnostic device 100 according to the first embodiment is not limited to the configuration illustrated in FIG. 2. For example, the configuration may be a configuration in which any of the elements are not needed or in which probe 101 has built-in transmitter 103, receiver 104, or a part of transmitter 103 and receiver 104.

Ultrasound diagnostic device 100 according to the first embodiment is characterized by transmitter 103, receiver 104, imaging signal generator 105, and imaging signal synthesizer 106 that constitute ultrasound signal processing device 150. For this reason, the configuration and functions of each of the elements of ultrasound signal processing device 150 is described herein. To the other configurations, the configuration of a widely used ultrasound diagnostic device can be applied. Thus, an existing ultrasound signal processing device 150 of a widely used ultrasound diagnostic device may be replaced with ultrasound signal processing device 150 according to the first embodiment, and the ultrasound diagnostic device may be used.

The configuration of probe 101 that is connected externally to ultrasound diagnostic device 100 and the configurations of ultrasound diagnostic device 100 other than the configuration of ultrasound signal processing device 150 are briefly described below.

Probe 101 has the plurality of transducers 101a arranged, for example, in a one-dimensional direction (hereinafter referred to as an "azimuthal direction"). Probe 101 converts pulsed electrical drive signals (hereinafter referred to as "drive pulse signals") supplied from transmitter 103 (described below) into pulsed ultrasound. Probe 101 transmits an ultrasound beam consisting of a plurality of ultrasounds emitted from the plurality of transducers toward an object to be measured with the outer surface of probe 101 adjacent to the transducer being in contact with the skin surface of the subject. Thereafter, probe 101 receives a plurality of ultrasounds reflected by the subject (hereinafter referred to as "reflected waves"), converts the reflected waves into electrical signals by the plurality of transducers, and supplies the electrical signals to receiver 104. According to the first embodiment, for example, probe 101 with 192 transducers 101a in a long shape is used. Note that transducers 101a may be arranged in a two-dimensional array.

Operation input unit 110 receives, for example, a command to instruct start of diagnosis and a variety of types of operational inputs, such as a variety of settings and operations input from an examiner to ultrasound diagnostic device 100 in order to input data (e.g., the personal information of an examinee). Thereafter, operation input unit 110 outputs the inputs to controller 109. For example, operation input unit 110 may be a touch panel configured as an integral part of display unit 108. In this case, the examiner can perform a variety of settings and operations on ultrasound diagnostic device 100 by touching the operation keys displayed on display unit 108 or performing dragging operations and, thus, ultrasound diagnostic device 100 is configured to be operable through the touch panel. Alternatively, operation input unit 110 may be, for example, a keyboard having keys for a variety of operations or an operation panel having buttons, levers, and the like for a variety of operations. Still alternatively, operation input unit 110 may be a mouse or the like for moving the cursor displayed on display unit 108. Yet still alternatively, the above-mentioned types of operation input units 110 may be used at the same time or may be combined into one.

Display unit 108 is a display unit for displaying images. Display unit 108 displays an image output from DSC 107 on the screen thereof. A liquid crystal display, a cathode-ray tube (CRT), an organic EL displays, or the like can be used as display unit 108.

Configuration of Ultrasound Signal Processing Device

The configurations of transmitter 103, receiver 104, imaging signal generator 105, and imaging signal synthesizer 106 that constitute ultrasound signal processing device 150 are described below.

Transmitter

Transmitter 103 is connected to probe 101 via cable 102. To transmit ultrasound from probe 101, transmitter 103 controls the point in time at which a high voltage is applied to the transmit transducers, which are all or a subset of transducers 101a of probe 101. Transmitter 103 selects a transmit transducer from among the plurality of transducers 101a of probe 101 and supplies a drive signal to the transmit transducer to transmit an ultrasound beam. Note that as used herein, the transmission unit of an ultrasound beam whose reflected wave is to be received after transmission is referred to as a "transmission event".

In ultrasound diagnostic device 100, transmitter 103 may have a configuration to select, from among the plurality of transducers 101a, a single transmit transducer Sx or a row of transmit transducers Sxq (q=1 to qmax, where q is a natural number) and causes the transmit transducers Sxq to transmit ultrasound beams in parallel. Alternatively, transmitter 103 may have a configuration to cause the transmit transducer Sxq to transmit a focused-wave ultrasound beam that is focused at the transmission focal point. Hereinafter, when a single transmit transducer Sx and a row of transmit transducers Sxq are not distinguished, the transmit transducers Sxq may be also referred to as a "transmit transducer Sx".

Figure 3:
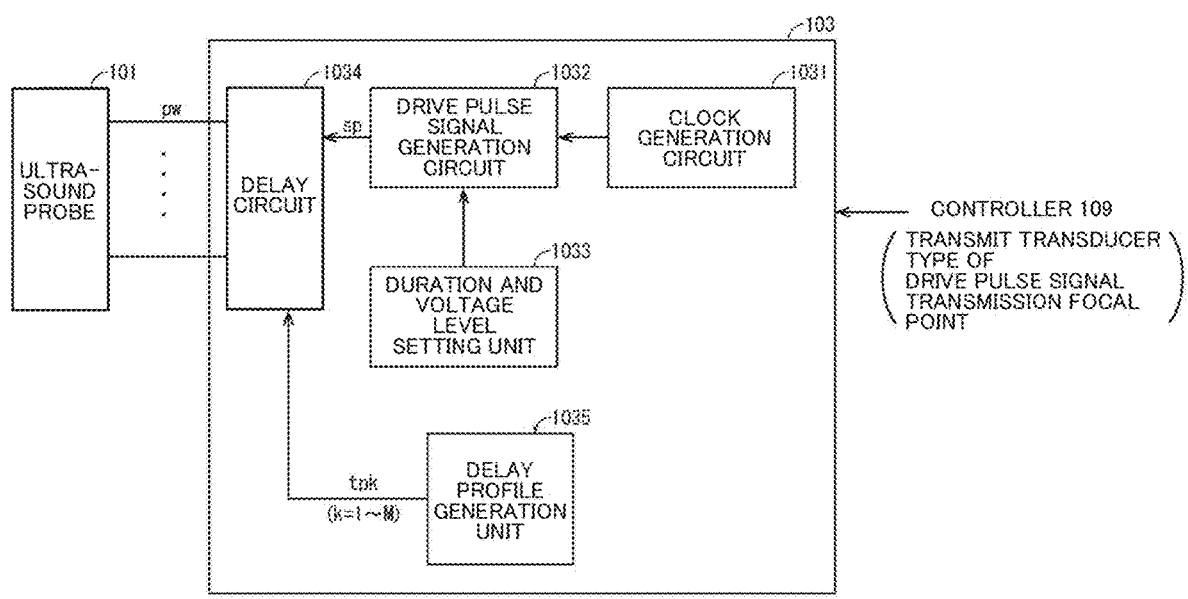
FIG. 3 is a functional block diagram illustrating the configuration of a transmitter of the ultrasound diagnostic device.
Figure 4A:
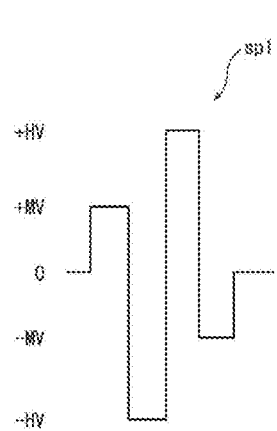
FIG. 4A illustrates an example of a drive pulse signal generated by the transmitter.
Figure 4B:
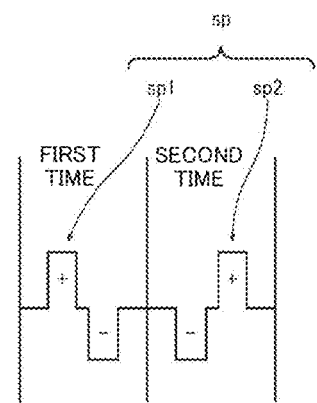
FIG. 4B illustrates an example of a drive pulse signal generated by the transmitter.
Figure 4C:
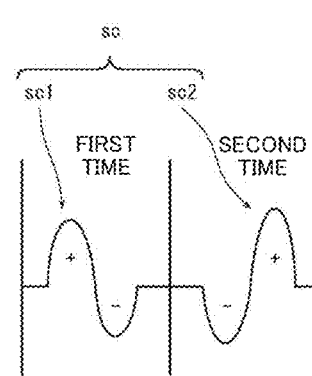
FIG. 4C is a schematic illustration of an example of a drive pulse signal according to another method.

FIG. 3 is a functional block diagram illustrating the configuration of transmitter 103. As illustrated in FIG. 3, transmitter 103 includes clock generation circuit 1031, drive pulse signal generation circuit 1032, a duration and voltage level setting unit 1033, delay circuit 1034, and delay profile generation unit 1035. FIGS. 4A and 4B are schematic illustrations of an example of a drive pulse signal sp, which is an example of a drive pulse signal generated in transmitter 103, and the way the phase inversion transmission is performed in pulse inversion. FIG. 4C illustrates the behavior of an example of a drive pulse signal sc generated by a different method. A drive pulse signal having a voltage level that steplessly varies, such as the drive pulse signal sc, may be obtained by a method for generating a drive pulse signal of any shape with a linear amplifier or may be obtained by performing, for example, bandwidth restriction processing on the drive pulse signal sp to smooth the drive pulse signal sp and outputting the signal as the drive pulse signal sc. As described above, either the method using a square-shaped signal as the drive pulse signal sc or the method using a drive pulse signal that varies steplessly, like the drive pulse signal sc, can be selected in accordance with the need.

Clock generation circuit 1031 is a circuit that generates a clock signal that serves as the minimum time unit for controlling the output timing and the duration of each of the voltage levels of the drive pulse signal sp.

Drive pulse signal generation circuit 1032 is a circuit that generates and outputs a drive pulse signal sp for transmitting an ultrasound beam to the transducer included in the transmit transducers Sx on the basis of the output from the duration and voltage level setting unit 1033.

In generating the drive pulse signal sp, drive pulse signal generation circuit 1032 generates the drive pulse signal sp based on a square wave by switching among five voltages (+HV/+MV/0 (GND)/−MV/−HV) or three voltages (+HV/0 (GND)/−HV) and outputting the voltage, as illustrated in FIG. 4A, for example. Note that the absolute value of the amplitude of the drive pulse signal, the polarity (positive or negative) of the voltage, and the number of voltage steps are not limited to those described above.

In ultrasound diagnostic device 100, for example, the pulse inversion method can be used to extract the harmonic components in THI. In this case, drive pulse signal generation circuit 1032 generates a pair of consecutive drive pulse signals sp1 and sp2 having inverted phases when the pulse inversion method is implemented. As a result, as illustrated in FIG. 4B, the first drive pulse signal sp1 and the second drive pulse signal sp2 generated by drive pulse signal generation circuit 1032 have inverted phases.

At this time, the first drive pulse signal sp1 and the second drive pulse signal sp2 may not be phase-inverted and may not have symmetrical shapes as needed. The shapes may be partially asymmetrical, and a linear signal component may be intentionally left and used.

Furthermore, the method for extracting harmonics is not limited to the method using phase inversion. For example, an existing method using amplitude modulation technique may be used.

In addition, in a method for calculating the reception results of a plurality of transmission events and extracting the required received signal components, the number of transmission events is not limited to two. Three or more transmission events may be sent. For example, the results of reception of three transmission events having phases shifted by 120° from each other may be synthesized to extract the third harmonic component.

To determine the transmission timing of the ultrasound beam when transmitting a focused-wave ultrasound beam, delay profile generation unit 1035 sets a delay time tpk (k is a natural number from 1 to M, where M is the number of transmit transducers) for each of the transducers on the basis of the information regarding the position of the transmit transducer Sx and the transmission focal point in the transmission control signal from controller 109. Thereafter, delay profile generation unit 1035 outputs the delay time tpk to delay circuit 1034. In this manner, the transmission of the ultrasound beam is delayed for each of the transducers by the delay time, and electronic focusing of the ultrasound beam is performed. Note that in the configuration in which ultrasound beams are transmitted in parallel from the transmit transducers Sx, a common delay time tpk is set for all of the transducers Sx.

Delay circuit 1034 is a circuit that sets a delay time for each of the transducers on the basis of a delay profile for the transmission timing of a transmission pulse when transmitting a focused-wave ultrasound beam. Thus, delay circuit 1034 delays the transmission of the drive signal by the set delay time to focus the transmit ultrasound beams. As a result, an ultrasound beam is transmitted from the transmit transducer Sx so that the ultrasound beam is focused on a specific part of the subject corresponding to the transmission focal point. Note that in the configuration in which ultrasound beams are transmitted in parallel from the transmit transducers Sx, a common delay time tpk is set for all of the transducers Sx.

The transmission sequence of a transmit wave from transmitter 103 is described below.

FIG. 5 illustrates the transmission sequence at transmitter 103. In FIG. 5, the transmission order L refers to the chronological order in which transmit waves are sent, and the scan line number i refers to a number corresponding to the position in the direction (X direction) of a scan line for which the line data of the acoustic line signal is generated by a phasing addition process.

According to the pulse inversion method, as described above, a set transmission is performed in which the transmission lines are the same for the same scan line, the transmission is driven by a pair of successive drive pulse signals having phases inverted from each other, and the harmonic signals are extracted from a pair of received signals obtained from the reflected waves to generate the line data of the acoustic line signal. As used herein, the term "transmission line" is an imaginary line that indicates the position of the ultrasound beam in the transmit wave. For example, the central axis of the ultrasound beam of the transmit wave may be defined as the transmission line.

A transmit wave type q in FIG. 5 denotes the polarities of a pair of transmit waves transmitted in the pulse inversion method. The transmit waves Tx1 and Tx2, which are connected by the symbol "+", indicate the transmit waves of positive and negative polarity that are transmitted in a set transmission on the basis of the drive pulse signals sp1 and sp2 in FIG. 4B or the drive pulse signals sc1 and sc2 in FIG. 4C, respectively.

According to the transmission sequence illustrated in FIG. 5, controller 109 outputs, to transmitter 103, a transmission control signal including information about the type of the transmit transducer Sx and a drive pulse signal (and, if necessary, information about the transmission focal point), corresponding to the scan line number i and transmit wave type q, for each transmission order L. Transmitter 103 performs the transmission process on the basis of the transmission control signal.

As illustrated in FIG. 5, the transmit waves Tx1$_i$ and Tx2$_i$, which constitute a set transmission of scan line number 1, and the transmit waves Tx1$_{97}$ and Tx2$_{97}$, which constitute a set transmission of scan line number 97, are transmitted alternately with each other. More specifically, the transmission of transmit wave Tx1$_{97}$ is performed between the transmissions of transmit waves Tx1$_1$ and Tx2$_1$, and the transmission of transmit wave Tx2$_1$ is performed between the transmissions of transmit waves Tx1$_{97}$ and Tx2$_{97}$. In addition, according to the transmission order L (L=1 to 385), the transmit waves Tx1 and Tx2 that constitute the set transmissions of scan line numbers 1 to 96 and the transmit waves Tx1 and Tx2 that constitute the set transmissions of scan line numbers 97 to 192 are transmitted alternately with each other.

Figure 6:
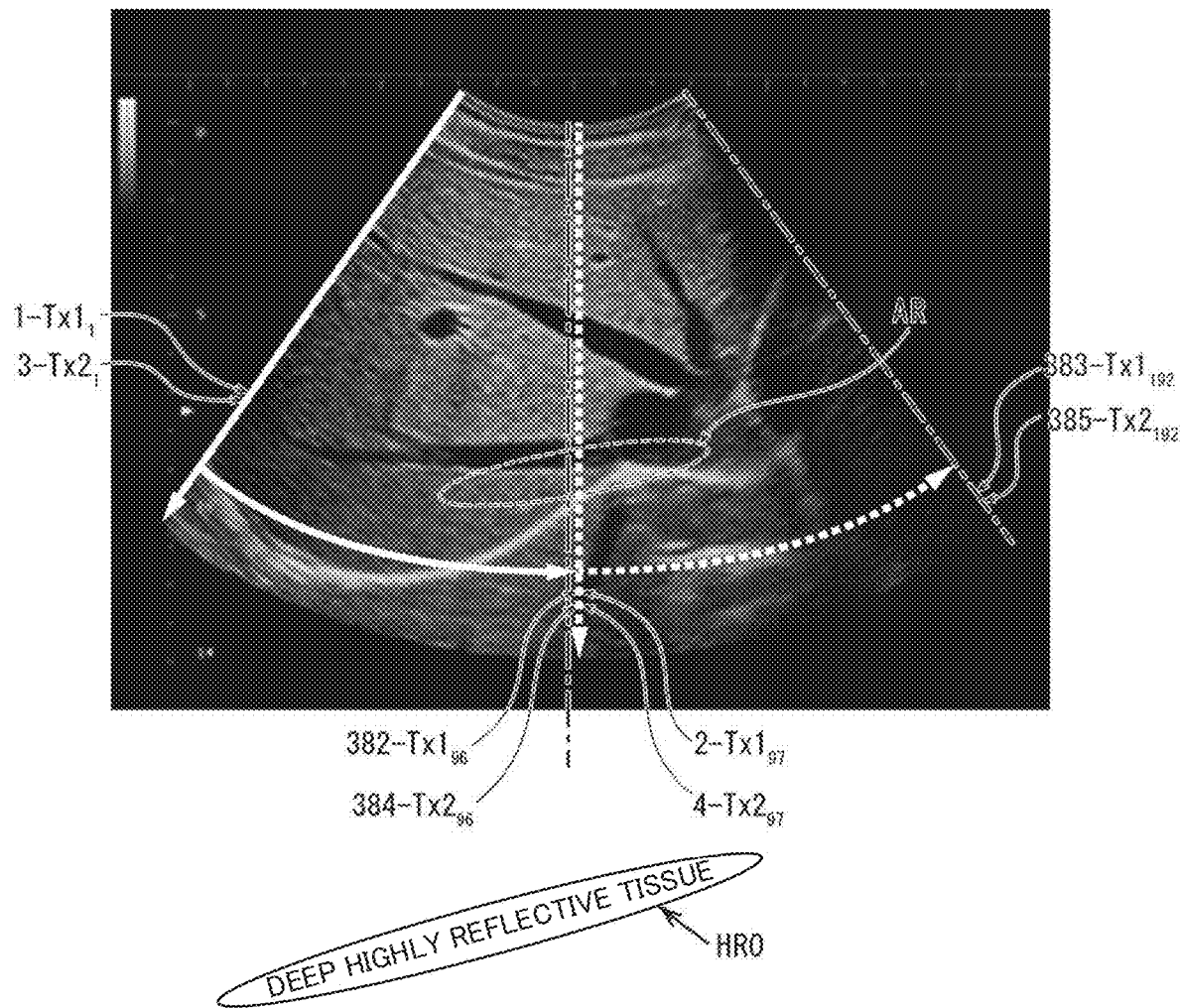
FIG. 6 is a schematic illustration of the propagation path of an ultrasound beam transmitted by the transmitter in the cross section of the subject.
Figure 7:
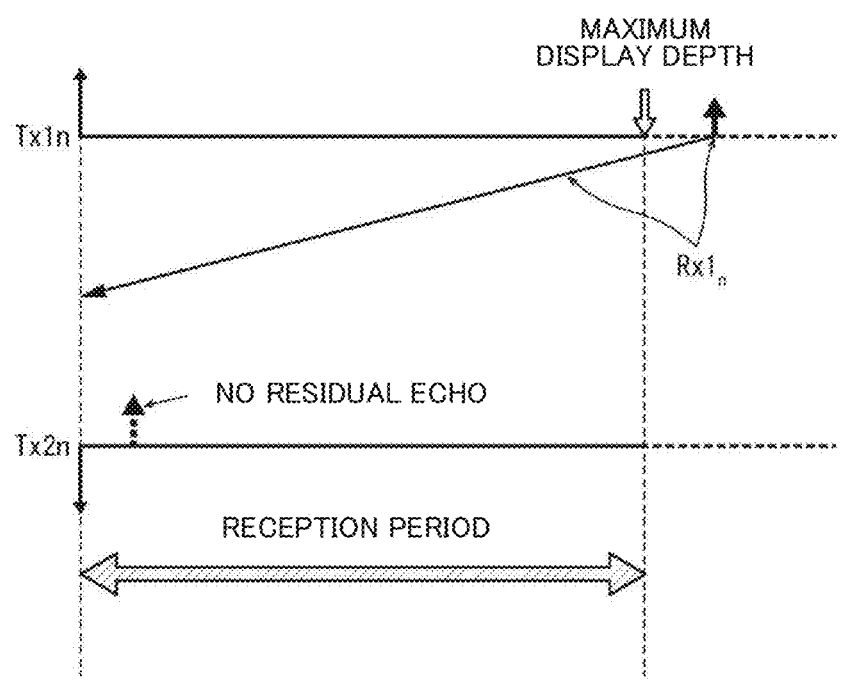
FIG. 7 is a schematic illustration of the way a reflected wave based on a transmitted ultrasound beam reaches a transducer in the ultrasound diagnostic device.

FIG. 6 is a schematic illustration of a propagation path of an ultrasound beam transmitted by transmitter 103 in a cross section of a subject. FIG. 7 is a schematic illustration of the way the reflected wave based on a transmit ultrasound beam reaches a transducer.

As described above, in a pair of set transmissions each performed for the same scan line, by transmitting one of the transmit waves Tx1 and Tx2 in a second set transmission between a pair of transmit/receive events of the transmit waves Tx1 and Tx2 in a first set transmission, the time interval between the transmit waves Tx1 and Tx2 in a set transmissions can be increased while preventing an increase in the pulse repetition period. As a result, as illustrated in FIG. 7, it is possible to prevent coupling of the reflected wave Rx1$_n$ from the deep highly reflective tissue based on the earlier transmit wave Tx1$_n$ into the reception result of the later transmit wave Tx2$_n$ performed for the same scan line (scan line number n), without increasing the frame rate. Thus, it can be prevented that the reflected wave Rx1$_n$ is detected as residual echo and is displayed in the display region as an artifact AR.

In addition, as illustrated in FIG. 6, since the propagation paths in the cross section of a subject are sufficiently separated between the scan lines of scan line number 1 and scan line number 97, for which transmission are successively performed, it is possible to prevent coupling of the reflected wave from the deep highly reflective tissue based on the immediately preceding transmit wave into the reception result of the current transmit wave. Thus, it can be prevented that the reflected wave is detected and is displayed in the display region as the artifact AR.

Receiver

Figure 8:
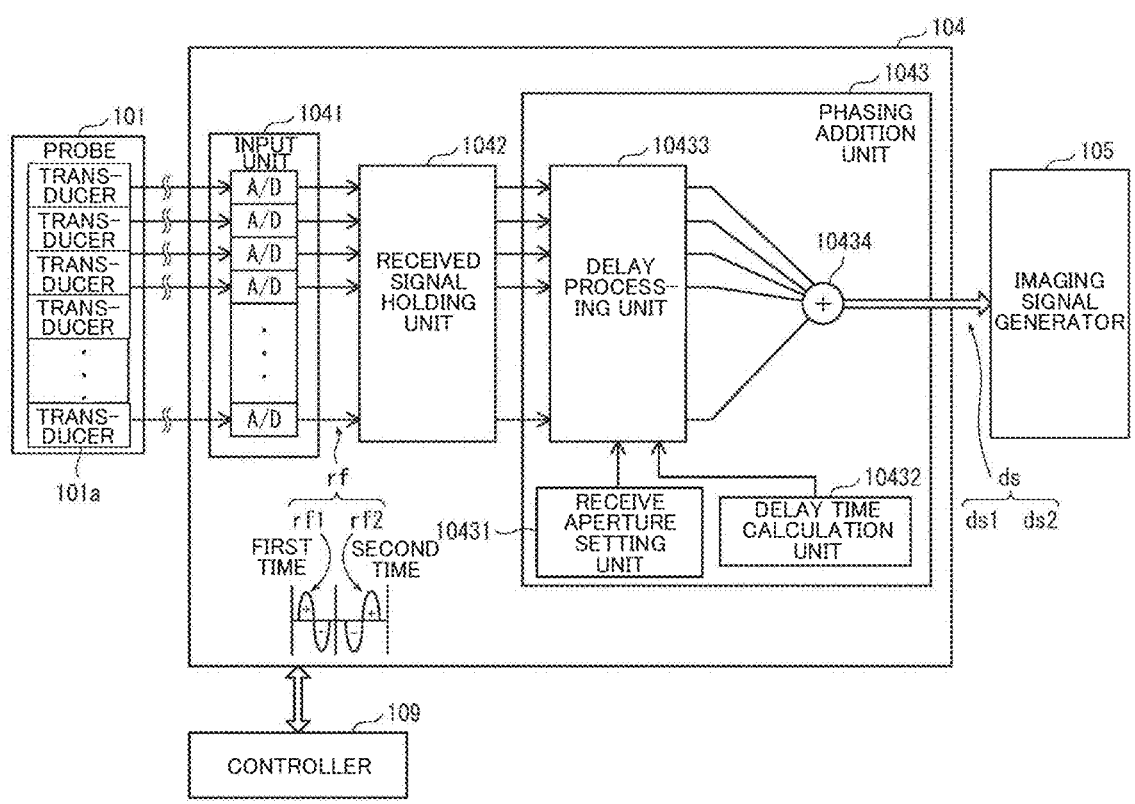
FIG. 8 is a functional block diagram of the receiver of the ultrasound diagnostic device.

Receiver 104 generates an acoustic line signal from the electrical signals obtained by the plurality of transducers 101a on the basis of the reflected ultrasound wave that is received by probe 101. Note that the term "acoustic line signal" refers to a received signal for a certain observation point after the phasing addition process is performed. The phasing addition process is described in more detail below. FIG. 8 is a functional block diagram of receiver 104. As illustrated in FIG. 8, receiver 104 includes input unit 1041, received signal holding unit 1042, and phasing addition unit 1043.

The configuration of each of the units that constitute receiver 104 is described below.

Input unit 1041 is connected to probe 101 via cable 102. Input unit 1041 is a circuit that generates a received signal (an RF signal) by amplifying an electrical signal obtained by receiving an ultrasound reflected wave in probe 101 in synchronization with a transmission event and AD-converting the electrical signal. Input unit 1041 generates time-series received signals in the order of transmission events and outputs the received signals to received signal holding unit 1042, which holds the received signals.

Note that the received signal (the RF signal) is a digital signal obtained by A/D converting the electrical signal converted from the reflected ultrasound wave received by each of the transducers. The received signal forms a series of signals arranged in the transmission direction (the depth direction of the subject) of the ultrasound wave received by each of the transducers.

When the pulse inversion method is implemented, input unit 1041 receives a pair of rf signals rf1 and rf2 with an inverted phase on the basis of reflected waves from a pair of drive pulse signals sp1 and sp2 or a pair of drive pulse signals sc1 and sc2 with inverted polarity transmitted for the same scan line at a time interval.

Input unit 1041 generates a sequence of received signals for each of lined-up receive transducers Rw, which are a subset or all of the N transducers 101a of probe 101, on the basis of the reflected ultrasound wave obtained by the receive transducer Rw in synchronization with the transmission event. The receive transducer Rw is selected on the basis of an instruction of controller 109. According to the first embodiment, the number of the receive transducers Rw is set to N, which is the total number of transducers 101a of probe 101. Note that the center of a row Rwx formed by the receive transducers Rw may be selected so as to match the transmit transducer Sx, and the number of receive transducers Rw may be greater than the number of transmit transducers.

Received signal holding unit 1042 is a computer-readable storage medium. For example, a semiconductor memory can be used as received signal holding unit 1042. Received signal holding unit 1042 may receive, from input unit 1041, a sequence of received signals for each of the receive transducers in synchronization with a transmission event and hold it until a single ultrasound image is generated. For example, a hard disk, an MO, a DVD, a DVD-RAM, or the like may be used as received signal holding unit 1042. Received signal holding unit 1042 may be a storage device externally connected to ultrasound diagnostic device 100. Alternatively, received signal holding unit 1042 may be a part of the data storage.

Phasing addition unit 1043 is a circuit that generates acoustic line signals by performing, in synchronization with the transmission event, a phasing addition process on the received signal sequences received by each of the receive transducers at a plurality of observation points that exist within the to-be-calculation scan line Bxi (hereinafter also referred to as a "scan line Bxi") in the subject. As used herein, the term "scan line Bxi" is one of scan lines for each of which the line data of the acoustic line signal is to be generated by the phasing addition process, and i represents an index corresponding to the position of scan line Bx in the X direction.

As illustrated in FIG. 8, phasing addition unit 1043 includes receive aperture setting unit 10431, delay time calculation unit 10432, delay processing unit 10433, and adder unit 10434. The configuration of each of the units is described below.

Receive aperture setting unit 10431 is a circuit that sets a scan line Bxi in the range to be analyzed in the subject and sets a receive aperture Rx for an observation point Pij on the scan line Bxi for which the acoustic line signal is to be calculated, on the basis of the position of the observation point Pij. As used herein, the term "receive aperture Rx" refers to a row of transducers selected from the row of transducers that have received the received signal and, in addition, is the row of transducers that received the received signal to be calculated when the received signal sequence based on the reflected wave from the observation point is subjected to a phasing addition process. In addition, hereinafter, the observation point P is also denoted as Pij when the observation point P is denoted with the indices i and j corresponding to the coordinates in the X and Y directions. In the phasing addition process, the delay time for the arrival of the reflected wave from the observation point Pij to each of the receive transducers in the receive aperture Rx is calculated, and the acoustic line signal is calculated on the basis of the delay time calculated for the observation point Pij.

Delay time calculation unit 10432 is a circuit that calculates the delay time for the arrival of reflected waves from the observation point Pij to each of the receive transducers in the receive aperture Rx for a plurality of observation points Pij in the scan line Bxi corresponding to the range to be analyzed in the subject.

The transmit wave emitted from the transmit transducer Sx reaches the observation point Pij, generates a reflected wave at the observation point Pij in accordance with a change in acoustic impedance. The reflected wave returns to the transducer Rw in the receive aperture Rx of probe 101. The length of the path to any observation point Pij and the length of the path from the observation point P to each of the receive transducers Rw can be calculated geometrically.

More specifically, the delay time for the observation point Pij is calculated in a manner described below.

For a plurality of observation points Pij in the scan line Bxi, delay time calculation unit 10432 calculates, from the sequence of received signals for the receive transducers Rw in the receive aperture Rx, the difference (the amount of delay) in reflected ultrasound wave arrival time to each of the receive transducers Rw by dividing the difference in distance between each of the observation points Pij and the receive transducer Rw by the sound speed value Cs.

Delay processing unit 10433 is a circuit that generates an acoustic line signal ds for the observation point Pij using a reference delay time for each of the receive transducers Rw.

Delay processing unit 10433 calculates the arrival time of the reflected wave from each of the observation points Pij to each of the receive transducers Rw on the basis of the arrival time difference (the amount of delay) calculated by delay time calculation unit 10432 and identifies the reflected wave as a received signal corresponding to the receive transducer Rw on the basis of the reflected wave arrival time. Delay processing unit 10433 performs the process for all of the observation points Pij included in the scan line Bxi and calculates the amount of delay Δtk for each of receive transducers Rwk to identify the received signal.

Adder unit 10434 is a circuit that receives, as input, the received signal that is identified corresponding to each of the receive transducers Rwk and that is output from delay processing unit 10433 and sums the received signals to generate an acoustic line signal subjected to a phasing addition process for the observation point P. Alternatively, adder unit 10434 may generate an acoustic line signal for the observation point P by multiplying the received signal identified for each of the receive transducers Rw by a weight sequence (receive apodization) for the receive transducer Rw and summing the resultant received signals. In this case, it is desirable that the weight sequences have symmetrical distribution around the transmit focus point F so that the weight for the transducer located at the center in the row direction of the receive aperture Rx is maximized.

By compensating for the delay time of the received signal detected by each of the receive transducer Rw located in the receive aperture Rx in delay processing unit 10433 and performing the addition process in adder unit 10434, the received signal from the observation point Pij can be extracted. In this manner, delay processing unit 10433 generates the acoustic line signals for all of the observation points P in the scan line Bxi. Thereafter, by gradually moving the scan line Bxij to be calculated in the azimuthal direction on the basis of the manner illustrated in FIG. 5, the ultrasound transmission is repeated while changing the position in the azimuthal direction. Thus, the acoustic line signals are generated for all observation points Pij in the scan line Bxi and are gradually output to imaging signal generator 105.

Imaging Signal Generator

Imaging signal generator 105 converts the line data and the like of each of the acoustic line signals corresponding to respective scan lines Bxi into a luminance signal corresponding to the intensity thereof, and performs a coordinate transformation on the luminance signal to the Cartesian coordinate system. Thus, imaging signal generator 105 generates the line data and the like of the ultrasound imaging signal. Imaging signal generator 105 performs this process sequentially for each of the plurality of scan lines Bxi and outputs the generated line data of the ultrasound imaging signal sequentially to imaging signal synthesizer 106, for example. More specifically, imaging signal generator 105 extracts the harmonic components of the acoustic line signals obtained from phasing addition unit 1043 by using the pulse inversion method to generate wideband acoustic line signal. Thereafter, imaging signal generator 105 performs processes such as envelope detection and logarithmic compression to perform luminance conversion. Subsequently, imaging signal generator 105 performs coordinate transformation on the luminance signal to the Cartesian coordinate system to generate the line data and the like of the ultrasound imaging signal. The ultrasound imaging signal may be a signal for a B-mode image, in which the intensity of the acoustic line signal is represented by the luminance.

In addition, as used herein, the term "ultrasound imaging signal" refers to a signal at each of stages at which the signal is displayed as an image generated on the basis of the acoustic line signal. An ultrasound imaging signal may include not only the luminance information at the final stage of imaging but also a received signal subjected to envelope detection at the preceding stage or the received signal further subjected to signal processing, such as bandpass filtering process, and the like.

Imaging signal generator 105 includes harmonic component extraction unit 105a. Harmonic component extraction unit 105a generates an ultrasound imaging signal from the harmonic components extracted by the pulse inversion method.

At this time, harmonic component extraction unit 105a extracts the harmonic components by performing a pulse inversion method on the acoustic line signal output from receiver 104, as described in, for example, Japanese Patent Application Laid-Open No. 2015-112261. Thereafter, among the harmonic components, the even-order harmonic components can be extracted by, as described above, summing the acoustic line signals based on a pair of phase-inverted rf signals rf1 and rf2 based on reflected waves corresponding to two transmit ultrasound waves generated from a pair of polarity-inverted drive pulse signals sp1 and sp2 transmitted at a time interval on the same scan line. That is, by summing the acoustic line signals, the fundamental harmonic component in the received signal can be removed, and even-order harmonic components can be extracted. The odd-order harmonic components, which are used as needed, can be extracted by subtracting the acoustic line signals based on the pair of rf signals rf1 and rf1 to remove even-order harmonic components and, thereafter, performing a filtering process as needed. If the odd-order harmonics are used, a wideband acoustic line signal can be obtained by performing a phase adjustment process on the extracted even-order and odd-order harmonic components with an all-pass filter or the like and, thereafter, performing summation.

Figure 9:
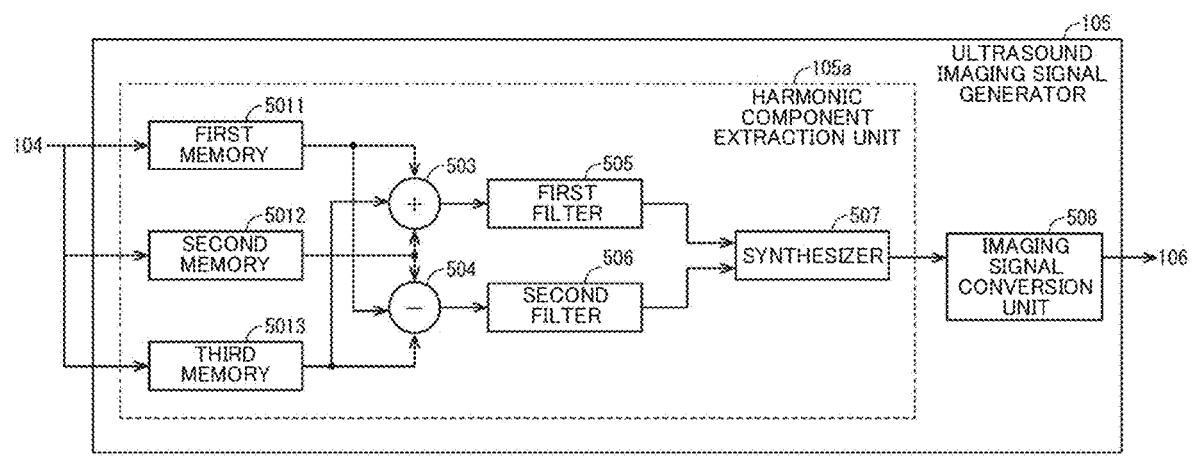
FIG. 9 is a functional block diagram of the configuration of an imaging signal generator of the ultrasound diagnostic device.

FIG. 9 is a functional block diagram illustrating the circuit configuration of imaging signal generator 105 of ultrasound diagnostic device 100. As illustrated in FIG. 9, imaging signal generator 105 includes harmonic component extraction unit 105a. Harmonic component extraction unit 105a has a configuration including first memory 5011, second memory 5012, third memory 5013, adder 503, subtractor 504, first filter 505, second filter 506, and synthesizer 507. Imaging signal generator 105 further includes imaging signal conversion unit 508.

According to the present embodiment, as described above, receiver 104 outputs, to imaging signal generator 105, the line data of the first acoustic line signal obtained by transmitting and receiving the transmit wave Tx1 and the line data of the second acoustic line signal obtained by transmitting and receiving the transmit wave Tx2 in accordance with the transmission order L illustrated in FIG. 5.

In harmonic component extraction unit 105a, the line data of the first acoustic line signal and the line data of the second acoustic line signal are stored in first memory 5011, second memory 5012, and third memory 5013 in accordance with the transmission order L.

Adder 503 selectively reads, from first memory 5011, second memory 5012, and third memory 5013, the line data of the first acoustic line signal and the line data of the second acoustic line signal acquired for the same scan line and sums the line data of the first acoustic line signal and the line data of the second acoustic line signal. Thus, adder 503 extracts the even-order harmonic component and outputs the even-order harmonic component to first filter 505. First filter 505 is a bandpass filter for removing noise components from the sum.

Subtractor 504 selectively reads, from first memory 5011, second memory 5012, and third memory 5013, the line data of the first acoustic line signal and the line data of the second acoustic line signal acquired for the same scan line. Thereafter, subtractor 504 subtracts the line data of the second acoustic line signal from the line data of the first acoustic line signal. Thus, subtractor 504 extracts and outputs the fundamental harmonic component and the odd-order harmonic component to second filter 506. Second filter 506 is a bandpass filter for removing the fundamental harmonic component from the subtraction result to extract the odd-order harmonic component.

By adding the even-order harmonic component output from first filter 505 to the odd-order harmonic component output from second filter 506, synthesizer 507 generates the line data of the acoustic line signal in which the fundamental harmonic component is removed and the harmonic components are included. Synthesizer 507 outputs the line data to imaging signal conversion unit 508.

Imaging signal conversion unit 508 performs envelope detection, logarithmic compression, and other processing to perform luminance conversion. Thereafter, imaging signal conversion unit 508 performs a coordinate transformation of the luminance signal to a Cartesian coordinate system to generate the line data of the ultrasound imaging signal and the like. Imaging signal conversion unit 508 outputs the line data and the like to imaging signal synthesizer 106.

Imaging Signal Synthesizer

Imaging signal synthesizer 106 is a circuit that synthesizes the line data of the ultrasound imaging signals corresponding to the plurality of scan lines Bxi output from imaging signal generator 105 by using the position of the observation point as a reference and generate the frame data and the like of an ultrasound image. As used herein, the term "frame" refers to one of blocks that form a collection of signals needed for constructing an ultrasound image. A synthesized acoustic line signal for one frame is called "frame data of an acoustic line signal".

Imaging signal synthesizer 106 includes image memory 106a composed of semiconductor memory, such as a DRAM and an SRAM included in integrated circuits. Imaging signal synthesizer 106 stores, for example, line data of ultrasound imaging signals corresponding to a plurality of scan lines Bxi output from imaging signal generator 105.

When storing, in image memory 106a, the line data of an ultrasound imaging signal corresponding to the scan line Bxi, imaging signal synthesizer 106 stores the acoustic line signal calculated for the observation point Pij in image memory 106a at an address corresponding to the position of the observation point Pij. In this way, imaging signal synthesizer 106 generates the frame data of the ultrasound image.

The synthesized frame data of the ultrasound image is output to DSC 107 and is displayed on display unit 108.

Operations

The ultrasound signal processing operation performed by ultrasound diagnostic device 100 having the above-described configuration is described below.

Overview of Processing Performed by Ultrasound Diagnostic Device

Figure 10:
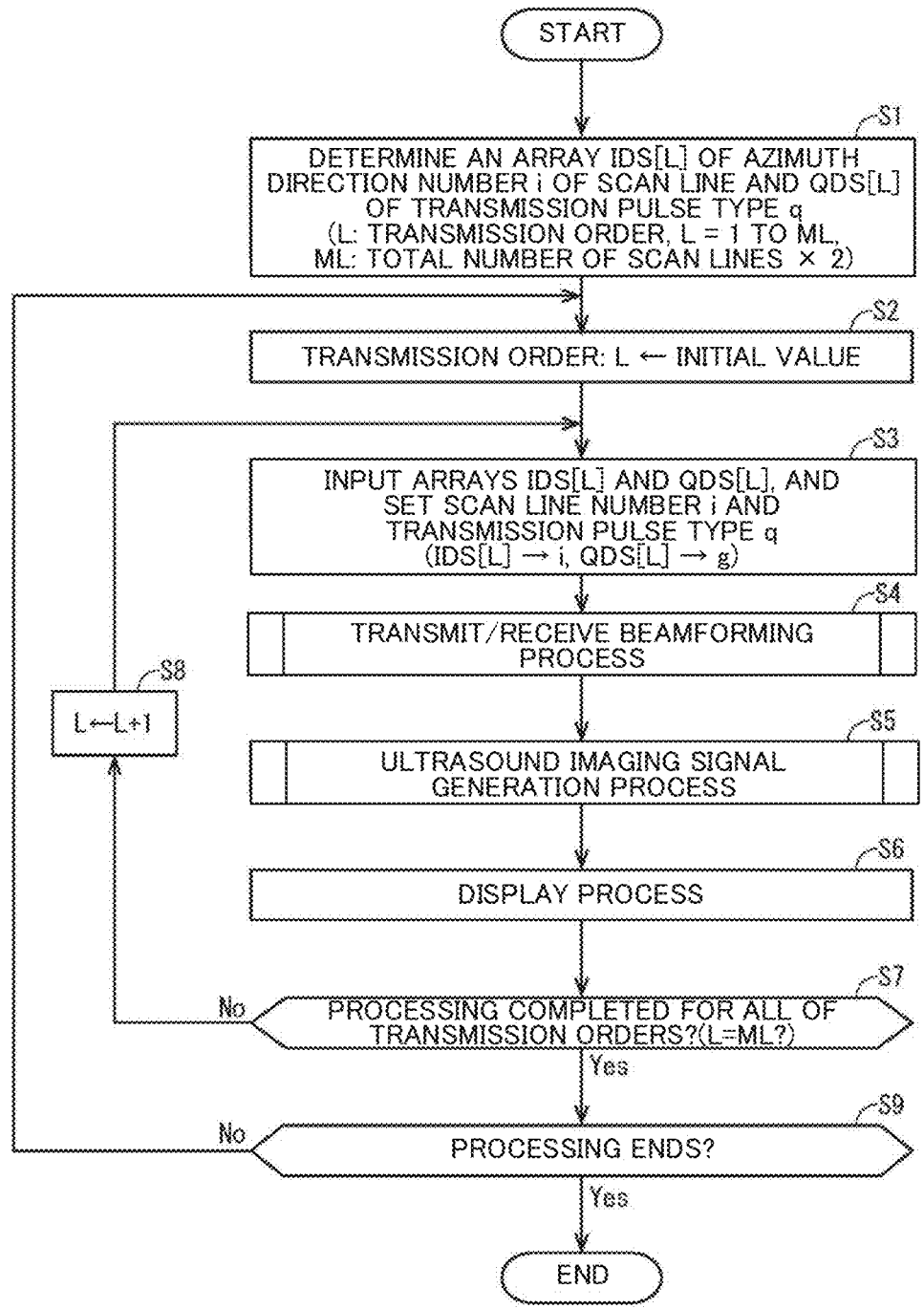
FIG. 10 is a flowchart illustrating the overview of the processing performed by the ultrasound diagnostic device.

FIG. 10 is a flowchart illustrating the overview of the ultrasound signal processing performed by ultrasound diagnostic device 100. That is, FIG. 10 is a flowchart illustrating the process performed in ultrasound diagnostic device 100 in the case where a transmit transducer Sx is gradually moved in the azimuthal direction, and a transmissions/reception event is performed ML times, which corresponds to twice the total number of scan lines to be scanned by using the pulse inversion method.

After start of ultrasonic inspection, controller 109 first determines an array IDS[L], which specifies the azimuth direction number I of a scan line and QDS[L], which specifies the transmission pulse type q, for the transmission order L (step S1), where L is an index representing the transmission order. Let ML be (the total number of scan lines×2). Then, L=1 to ML. The azimuth direction number I of a scan line corresponds to a transmission line, which indicates the position of the ultrasound beam to be transmitted.

Subsequently, controller 109 sets the transmission order L to an initial value (step S2), inputs the arrays IDS[L] and QDS[L] stored in the memory or the like, and sets the scan line number i and the transmission pulse type q (step S3).

For example, in the case of the transmission sequence illustrated in FIG. 5, the array IDS[L] (L=1 to 385)=[1, 97, 1, 97, 2, 98, 2, 98 . . . , 96, 192, 96, 192] and the array QDS[L] (L=1 to 385)=[Tx1, Tx1, Tx2, Tx2, Tx1, Tx1, Tx2, Tx2 Tx1, Tx1, Tx2, Tx2].

Subsequently, the transmit/receive beamforming process is performed in accordance with the flowchart illustrated in FIG. 11 (described below) (step S4). That is, transmitter 103 sets the position I of the azimuth direction of the transmit transducer Sx to the initial value and causes the transducers in the transmit transducers Sx to transmit an ultrasound beam. Receiver 104 generates the line data of the acoustic line signal corresponding to the scan line Bxi on the basis of the obtained reflected wave and outputs the line data to imaging signal generator 105.

Subsequently, in step S5, imaging signal generator 105 generates the line data of the ultrasound imaging signal from the line data of the acoustic line signal corresponding to the scan line Bxi, which is output from receiver 104, on the basis of the flowchart illustrated in FIG. 12 (described below). Furthermore, imaging signal synthesizer 106 may synthesize line data of the ultrasound imaging signals corresponding to the plurality of scan lines Bxi for the azimuthal positions of the transmit transducers Sx and generate frame data of the ultrasound image.

Subsequently, in step S6, DSC 107 generates a display image including the ultrasound image on the basis of the line data of the ultrasound imaging signal and causes display unit 108 to display the image.

Subsequently, DSC 107 determines whether the transmission order L is the maximum value ML (step S7). If the transmission order L is not the maximum value ML, DSC 107 increments L by one (step S8) and, thereafter, the processing returns to step S3. If the transmission order L is the maximum value ML, the display of ultrasound imaging signals has been completed for all of the scan lines Bxi. Accordingly, the processing proceeds to step S9, where the processing ends or returns to step S2 if the processing does not end.

Beamforming Process regarding Transmission and Reception

The processing operation in step S4 is described in detail below.

Figure 11:
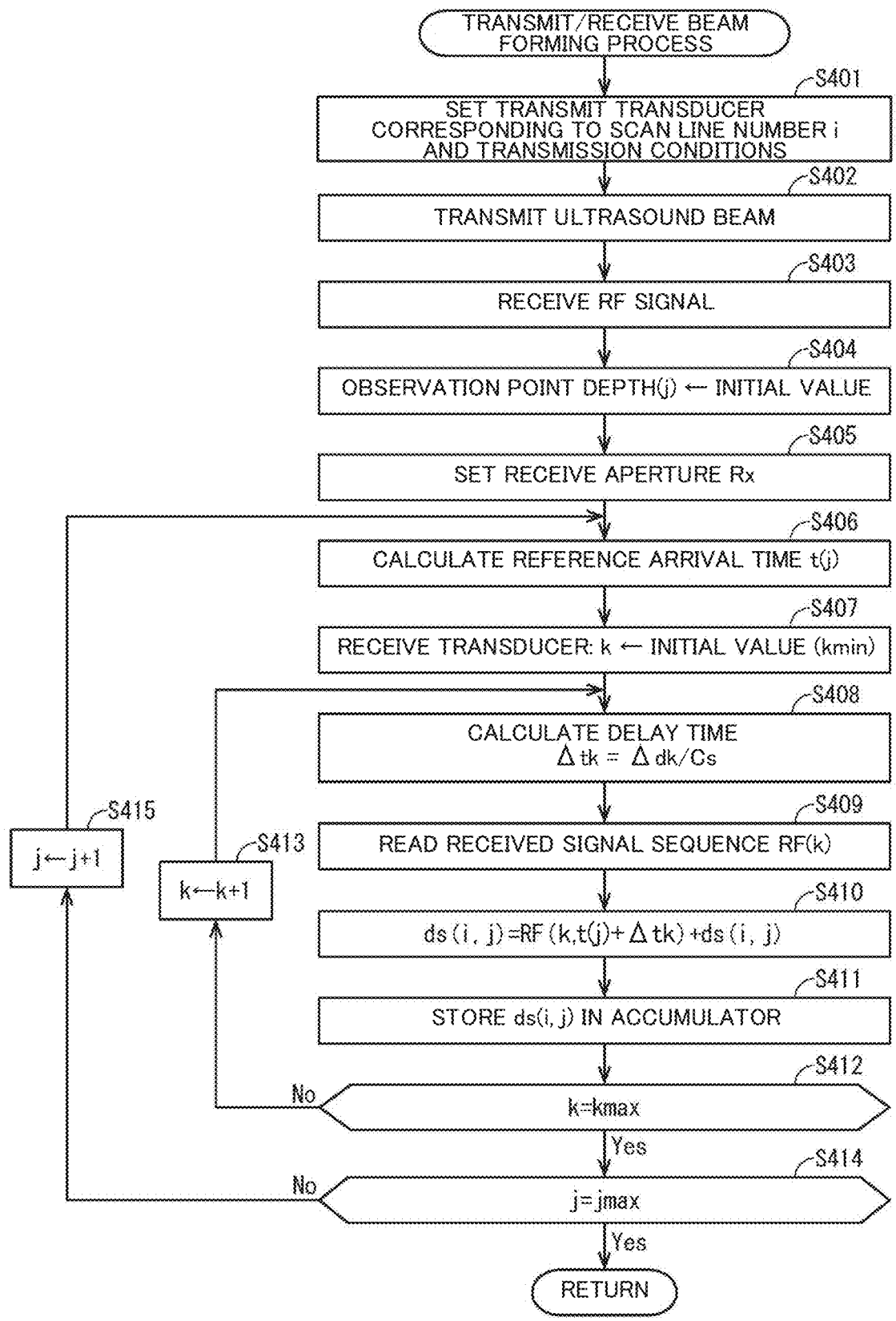
FIG. 11 is a flowchart illustrating the details of a transmit/receive beamforming process (step S4) illustrated in FIG. 10.

FIG. 11 is a flowchart illustrating the details of the transmit/receive beamforming process (step S4) in FIG. 10.

Controller 109 first outputs, to transmitter 103, a transmission control signal, such as information about the type of transmit resonator Sx and drive pulse signal (and, if necessary, information about the transmission focal point) corresponding to the scan line number i and transmit wave type q. Transmitter 103 sets the transmission conditions on the basis of the transmission control signal (step S401).

Subsequently, transmitter 103 performs a transmission process (a transmission event) in which a drive signal is supplied to the transmit transducer Sx to transmit an ultrasound beam (step S402).

Subsequently, input unit 1041 generates a received signal (an RF signal) on the basis of the electrical signal obtained through reception of the ultrasound reflected wave in probe 101 and outputs the received signal to received signal holding unit 1042 to hold the received signal in received signal holding unit 1042 (step S403).

Subsequently, for the observation point P(i, j) to be calculated first, input unit 1041 sets the index j representing the coordinate Yin the depth direction of the observation point P(i, j) to the initial value (step S404) and sets the row of the transducers that constitute the receive aperture Rx on the basis of the position of the scan line Bxi (step S405). For example, the receive aperture Rx may be set symmetrically with respect to the scan line passing through the observation point P(i, j).

Subsequently, delay time calculation unit 10432 calculates the reference arrival time t(j) (step S406). The reference arrival time t(j) is the time required for the ultrasound to travel a round trip between the observation point P (i, j) and the receive transducer Rw located at the center of the row of the receive aperture Rx.

Subsequently, delay time calculation unit 10432 sets the index k used to identify a receive transducer Rw in the receive aperture Rx to the initial value (step S407). In this example, as an example, the initial value is set to a minimum value kmin of the number of the receive transducers Rw (kmin to kmax) included in the receive aperture Rx.

Subsequently, delay time calculation unit 10432 calculates a delay time Δtk of the arrival of the reflected wave from the observation point P (i, j) for the receive transducer Rwk (step S408).

Subsequently, delay processing unit 10433 reads the received signal sequence RF(k) from received signal holding unit 1042 (step S409), identifies a received signal value RF(k, t(j)+Δtk) in the received signal sequence RF(k), calculates the sum of the received signal value RF(k, t(j)+Δtk) and the acoustic line signal ds(i, j) stored in an accumulator (step S410), and stores the new acoustic line signal ds(i, j) in the accumulator (step S411).

Thereafter, delay processing unit 10433 determines whether the index k that identifies the receive transducer Rw is the maximum value kmax (step S412). If the index k is not the maximum value kmax, the index k is incremented by one (step S413), and the processing returns to step S408. If the index k is the maximum value kmax of the number of the receive transducer Rw in the receive aperture Rx, delay processing unit 10433 determines whether calculation of the acoustic line signal dS(i, j) for the observation point P (i, j) is completed and j is the maximum value jmax (step S414). If the index j is not the maximum value jmax, delay processing unit 10433 increments j by one (step S415), and the processing returns to step S406. If the index j is the maximum value jmax, the calculation of the acoustic line signals dS(i, j) for all of the observation points P (i, j) located on the scan line Bxi is completed and, thus, the processing ends.

Ultrasound Imaging Signal Generation Process

The processing operation performed in step S5 is described in detail below.

Figure 12:
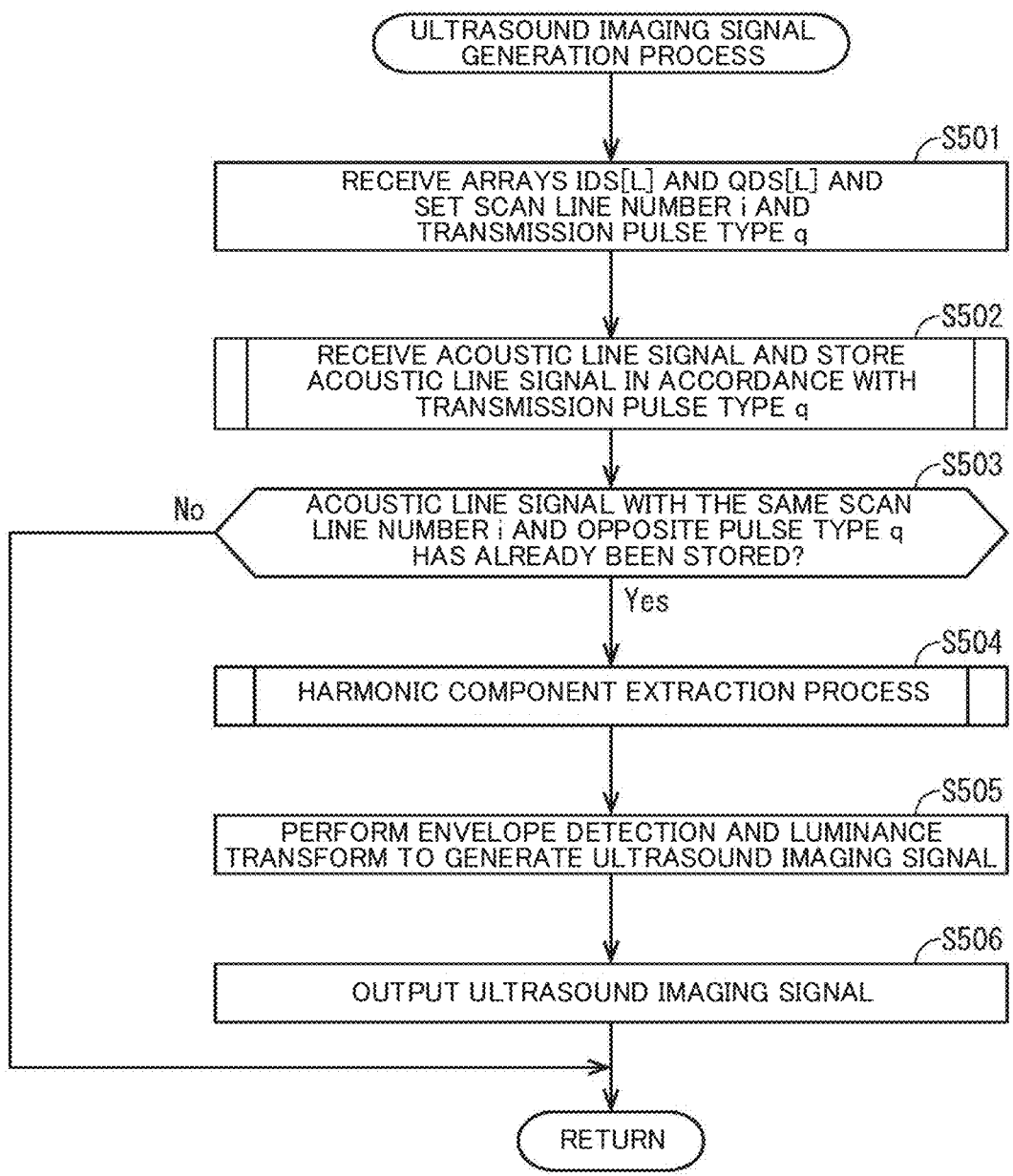
FIG. 12 is a flowchart illustrating the details of an ultrasound imaging signal generation process (step S5) illustrated in FIG. 10.

FIG. 12 is a flowchart illustrating the details of the ultrasound imaging signal generation process (step S5) in FIG. 10.

Controller 109 receives the arrays IDS[L] and QDS[L] stored in the memory or the like and sets the scan line number i and the transmission pulse type q (step S501). Subsequently, the line data of the acoustic line signal are stored in first memory 5011, second memory 5012, and third memory 5013 of harmonic component extraction unit 105a in accordance with the transmission order L (step S502). As used herein, the term "line data of the acoustic line signal" refers to either the line data of the first acoustic line signal or the line data of the second acoustic line signal.

Subsequently, for the stored line data of the acoustic line signal, controller 109 determines whether the acoustic line signal with the same scan line number i and opposite pulse type q has already been stored in any one of the memories (step S503). If not stored, the process in step S5 ends. However, if stored, the processing proceeds to step S504, where the harmonic component extraction process is performed.

Figure 13:
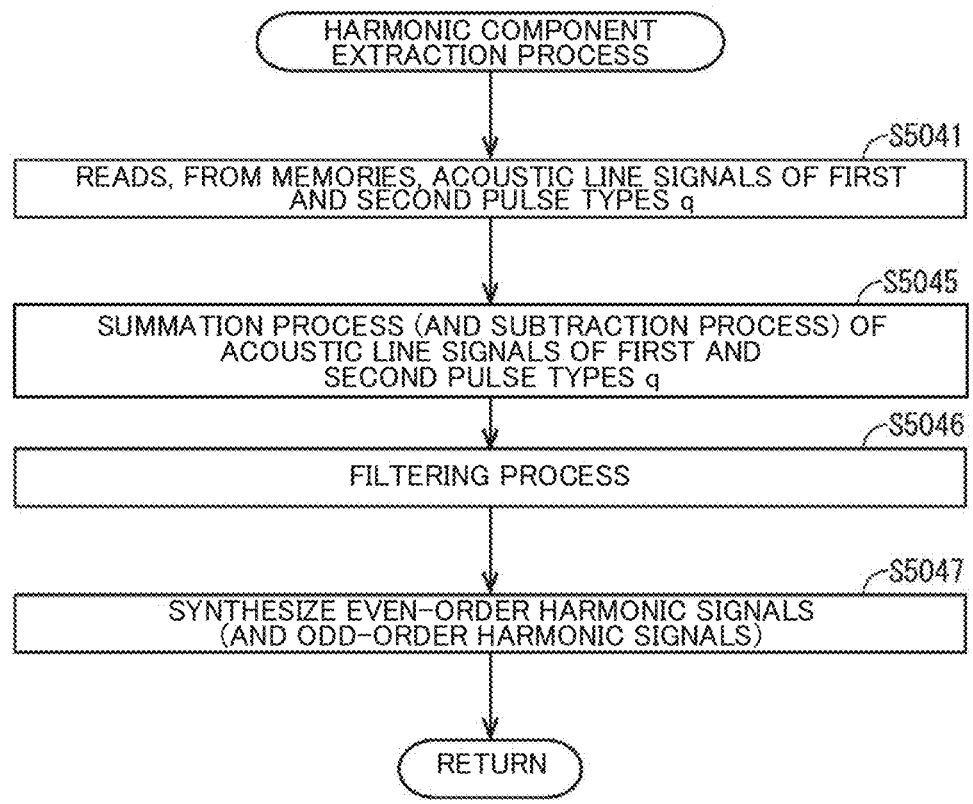
FIG. 13 is a flowchart illustrating the details of a harmonic component extraction process (step S504) illustrated in FIG. 12.

FIG. 13 is a flowchart of the details of the harmonic component extraction process (step S504) in FIG. 12.

Harmonic component extraction unit 105a selectively reads, from first memory 5011, second memory 5012, and third memory 5013, the acoustic line signals of the first and second pulse types q for the same scan line Bxi, that is, the first acoustic line signal and the second acoustic line signal (step S5041). Adder 503 sums the acoustic line signals of the first and second pulse types q to extract even-order harmonic component and, if necessary, subtractor 504 performs subtraction to extract odd-order harmonic component (step S5045). Thereafter, harmonic component extraction unit 105a removes the fundamental harmonic component from the subtraction result through a filtering process (step S5046) to extract only the odd-order harmonic component. Subsequently, harmonic component extraction unit 105a synthesizes the even-order harmonic signals and, if necessary, the extracted odd-order harmonic signals (step S5047) to generate the line data of the acoustic line signal containing the harmonic components and outputs the line data to imaging signal conversion unit 508.

Subsequently, in step S505 illustrated in FIG. 12, imaging signal conversion unit 508 performs envelope detection, logarithmic compression, and the like to perform luminance transform. Thereafter, imaging signal conversion unit 508 generates the line data of the ultrasound imaging signal and the like by performing coordinate transformation to the Cartesian coordinate system and outputs the line data and the like to imaging signal synthesizer 106 (step S506).

Brief Summary

As described above, according to ultrasound diagnostic device 100 of the first embodiment, in a pair of set transmissions each performed for the same scan line, by transmitting one of the transmit waves Tx1 and Tx2 in a second set transmission between a pair of transmit/receive events of the transmit waves Tx1 and Tx2 in a first set transmission, the time interval between the transmit waves Tx1 and Tx2 in a set transmissions can be increased while preventing an increase in the pulse repetition period. As a result, it is possible to prevent coupling of the reflected wave $Rx1_n$ based on the earlier transmit wave $Tx1_n$ into the reception result of the later transmit wave $Tx2_n$ performed for the same scan line, without increasing the frame rate. Thus, it can be prevented that the reflected wave $Rx1_n$ is detected as residual echo.

In addition, since the propagation paths of the scan lines consecutively transmitted in the cross-section of the subject are sufficiently separated, it is possible to prevent coupling of reflected waves from deep highly reflective tissue based on the immediately preceding transmit wave into the current transmit wave. Thus, detection of residual echo can be prevented.

First Modification

While ultrasound diagnostic device 100 has been described with reference to the first embodiment, the present disclosure is not limited in any way to the above-described first embodiment, except for its essential characteristic constituent elements. As an example of such a form, a modification of ultrasound diagnostic device 100 is described below.

In an ultrasound diagnostic device according to the first modification, the number of area divisions and the number of consecutive one-rate transmissions/reception events do not necessarily have to be the same. For example, a method in which four areas are sequentially transmitted and received in a one rate two consecutive mode may be employed. That is, there is no restriction on the number of area divisions, and division and scanning control can be performed as appropriate. For example, the deterrent effect of coupling of residual echoes increases with increasing distance between the spatial positions of the divided areas, but more system channels are required. In contrast, the deterrent effect of the coupling of residual echoes decreases with decreasing distance between the spatial positions of the divided areas, but the method can be applied even when the number of system channels is small.

FIG. 14 illustrates an example of a transmission sequence at transmitter 103 of the ultrasound diagnostic device according to the first modification. In the configuration illustrated in FIG. 14, the cross-section of the subject is divided into two areas in the azimuthal direction. For each area, set transmission is sequentially performed on the basis of a transmission sequence the same as that illustrated in FIG. 5 of ultrasound diagnostic device 100 according to the first embodiment.

Figure 15:
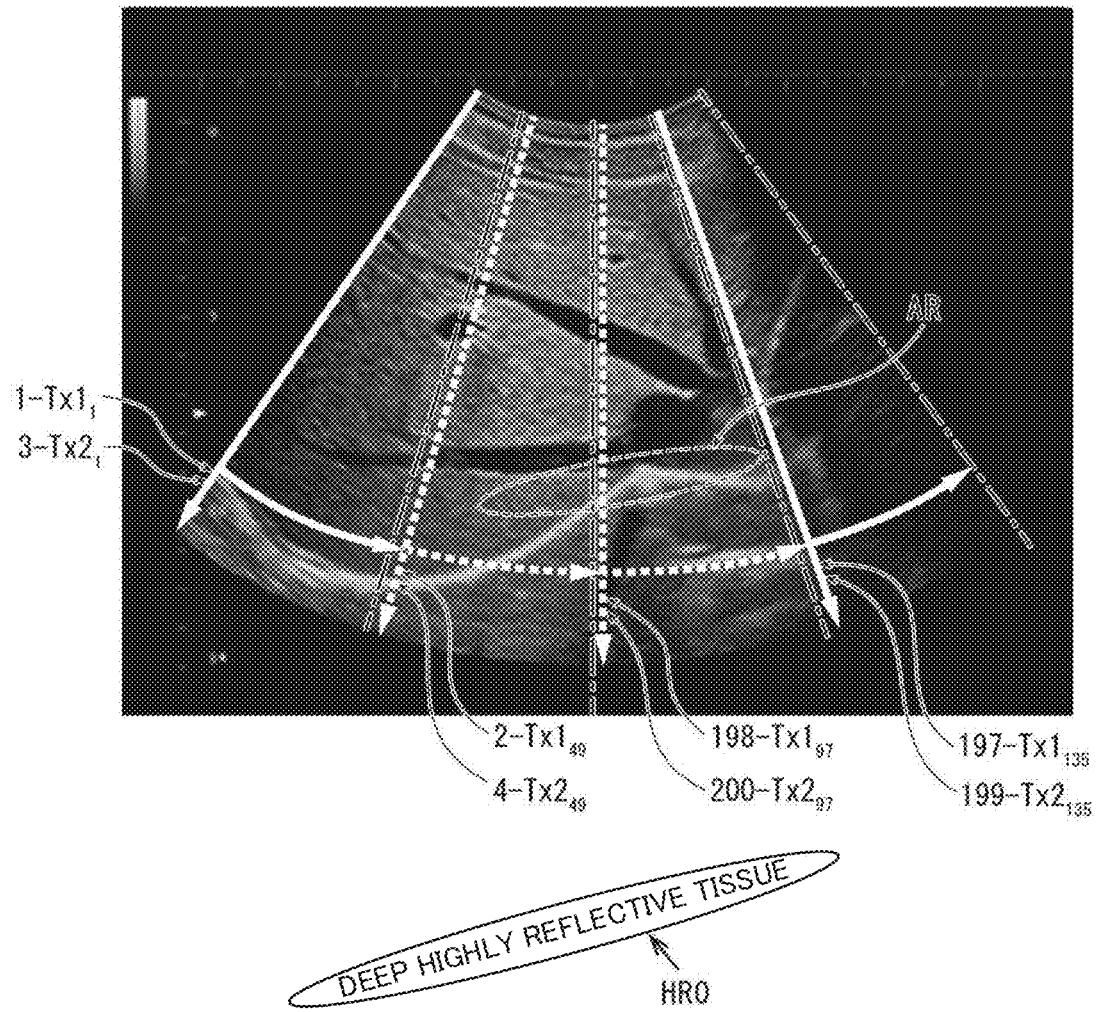
FIG. 15 is a schematic illustration of the propagation path of an ultrasound beam in the cross-section of a subject during transmission performed by the transmitter of the ultrasound diagnostic device according to the first modification.

More specifically, in the ultrasound diagnostic device according to the first modification, as illustrated in FIG. 15, in an area 1/2 located on the left side of the plane in the azimuthal direction of the subject cross-section, the transmit waves $Tx1_1$ and $Tx2_1$, which constitute the set transmission of scan line number 1, and the transmit waves $Tx1_{49}$ and $Tx2_{49}$, which constitute the set transmission of scan line number 49, are transmitted alternately with each other. More specifically, between the transmissions of transmit waves $Tx1_1$ and $Tx2_1$, the transmission of transmit wave $Tx1_{49}$ is performed. Between the transmissions of transmit waves $Tx1_{49}$ and $Tx2_{49}$, the transmission of transmit wave $Tx2_1$ is performed. In addition, according to the transmission order L (L=1 to 196), transmit waves Tx1 and Tx2, which constitute the set transmissions of scan line numbers 1 to 49, and the transmit waves Tx1 and Tx2, which constitute the set transmissions from scan line numbers 48 to 96, are transmitted alternately with each other.

Similarly, in an area 2/2, which is located on the right side of the plane in the azimuth direction of the subject cross-section, transmit waves $Tx1_{135}$ and $Tx2_{135}$, which constitute the set transmission of scan line number 135, and transmit waves $Tx1_{97}$ and $Tx2_{97}$, which constitute the set transmission of scan line number 97, are transmitted alternately with each other subsequent to transmission order L (L=1 to 196). Thereafter, according to the transmission order L (L=197 to 385), the transmit waves Tx1 and Tx2, which constitute the set transmission of scan line numbers 135 to 192, and the transmit waves Tx1 and Tx2, which constitute the set transmission of scan line numbers 97 to 134, are transmitted alternately with each other.

FIG. 15 is a schematic illustration of the propagation path of the ultrasound beam in the cross-section of a subject for transmission performed by transmitter 103 of the ultrasound diagnostic device according to the modification.

As described above, in a pair of set transmissions each performed for the same scan line, by transmitting one of the transmit waves Tx1 and Tx2 in a second set transmission between a pair of transmit/receive events of the transmit waves Tx1 and Tx2 in a first set transmission, the time interval between the transmit waves Tx1 and Tx2 in a set transmissions can be increased while preventing an increase in the pulse repetition period. As a result, like the first embodiment, it is possible to prevent coupling of the reflected wave $Rx1_n$ based on the first transmit wave $Tx1_n$ into the reception result of the second transmit wave $Tx2_n$ performed for the same scan line, without increasing the frame rate. Thus, it can be prevented that the reflected wave $Rx1_n$ is detected as residual echo.

In addition, as illustrated in FIG. 15, in a cross-section of the subject, the propagation paths of the scan lines of scan line number 1 and scan line number 49 or the propagation paths of the scan lines of scan line number 135 and scan line number 97 for which transmission is consecutively performed are sufficiently separated from each other. As a result, like the first embodiment, it is possible to prevent coupling of reflected waves from deep highly reflective tissue based on the previous transmit wave into the current transmit wave. Thus, detection of residual echo can be prevented.

Note that in the ultrasound diagnostic device according to the first modification, the number of area divisions, spatial positioning, and the number of one-rate consecutive transmissions/reception events are set and selected (including user selection) as appropriate in consideration of the shape of the probe, the scanning method (linear type, sector type, etc.), the frequency band of the probe, the transmission/reception frequency, the display depth, the part to be observed, other than the system requirements. At this time, it is desirable that the positions of the scan lines for one-rate two consecutive transmissions be separated by more than half the transmission aperture. In this way, the scan line for the second transmission in the first transmission-reception is set outside the transmission aperture of the first transmission in one-rate two consecutive transmissions. For this reason, coupling of the reflected wave caused by the first transmission in the first transmission-reception can be effectively prevented.

Second Embodiment

Overview

In a method according to the second embodiment, among multiple rate transmission and reception, the time interval between the first transmission and reception (transmission and reception based on transmit wave Tx1) and the second transmission and reception (transmission and reception based on transmit wave Tx2) is set to be sufficiently long, and the time interval between the transmission and reception based on transmit wave Tx2 and the transmission and reception based on transmit wave Tx1 for the adjacent scan line is set to be short.

The method according to the second embodiment, coupling of residual echo from the adjacent scan line cannot be prevented. Accordingly, residual echo originating from a membranous hyperechoic tissue located substantially perpendicular to the transmit direction cannot be removed. However, because the Tx1-to-Tx2 mixture can be prevented by a simplified technique of changing the transmission interval, residual echo from a non-membranous and non-contiguous tissue can be prevented. In addition, the frame rate can be improved as compared with the case where both transmission and reception using the transmit wave Tx1 and transmission and reception using the transmit wave Tx2 are performed at sufficiently long time intervals.

Furthermore, preferably, by varying the interval between the transmission and reception based on the transmit wave Tx2 and the transmission and reception based on the transmit wave Tx1 for the adjacent scan line frame by frame a plurality of times, it is possible to disperse the mixture positions of the residual echoes from the adjacent scan line to multiple positions and, thus, to reduce the effect of residual echo virtual image during, for example, frame average display which is normally performed.

Particular Example

Ultrasound diagnostic device 100 according to the first embodiment has a configuration in which by using the pulse inversion technique, the transmit waves $Tx1_1$ and $Tx2_1$, which constitute the set transmission for the first scan line and the transmit waves $Tx1_{97}$ and $Tx2_{97}$, which constitute the set transmission for the second scan line that are separated from the first scan line by more than a predetermined distance in the azimuthal direction, are transmitted alternately with each other in accordance with the transmission sequence illustrated in FIG. 5.

In contrast, the ultrasound diagnostic device according to the second embodiment is characterized in that the transmission sequence differs from that in ultrasound diagnostic device 100 according to the first embodiment and in that the transmit waves Tx1 and Tx2 constituting the set transmission of the pulse inversion method are transmitted sequentially and alternately at alternate different time intervals (Tx1 to Tx2, Tx2 to Tx1), and the time interval between the transmit waves $Tx1_1$ and $Tx2_1$ constituting the set transmission for the same scan line i, is sufficiently long to prevent coupling of residual echoes in the reflected wave for the transmit wave $Tx2_1$.

Figure 17:
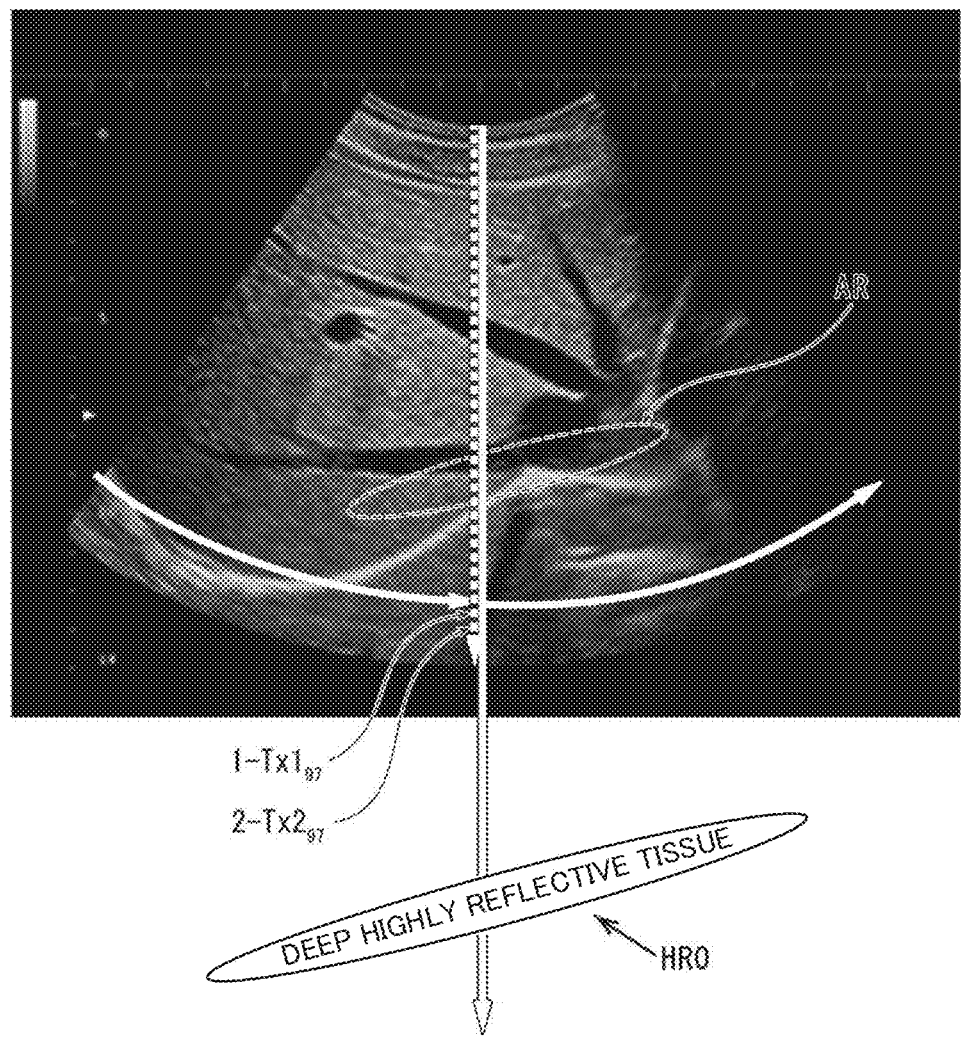
FIG. 17 is a schematic illustration of a propagation path of an ultrasound beam in a cross-section of a subject during transmission performed by the transmitter of the ultrasound diagnostic device according to the second embodiment.

FIG. 16 illustrates the transmission sequence at transmitter 103 of the ultrasound diagnostic device according to the second embodiment. FIG. 17 is a schematic illustration of a propagation path of an ultrasound beam in a cross-section of a subject during transmission performed by transmitter 103 of the ultrasound diagnostic device according to the second embodiment.

In FIG. 16, the meanings of transmission order L, scan line number i, and transmit wave type q are the same as those in FIG. 5. Let transmit waves $Tx1_i$ and $Tx2_i$ denote a pair of transmit waves that constitute a set transmission for scan line number i and have a common transmission line. Then, the transmit waves $Tx1_i$ and $Tx2_i$ connected by the symbol "+" are transmitted in a set transmission by the pulse inversion method. More specifically, as illustrated in FIGS. 15 and 16, in accordance with the transmission order L (L=1 to 385), the transmit waves Tx1 and Tx2, which constitute the set transmissions of scan line number 1 to 192 and have a common transmission line, are transmitted sequentially and alternately. At this time, the ultrasound diagnostic device according to the second embodiment is characterized in that a time interval T1 between the transmit waves $Tx1_i$ and $Tx2_i$ in the set transmission of scan line number i is longer than a time interval T2 between the transmit wave $Tx2_i$ in the set transmission of scan line number i and the transmit wave $Tx1_{i+1}$ in the set transmission of scan line number i+1. Note that the time interval T1 between the transmissions of transmit waves $Tx1_i$ and $Tx2_i$ is long enough that the reflected wave Rx1i from the deep highly reflective tissue based on the earlier transmit wave $Tx1_i$ does not reach the transducer during the reception period for the later transmit wave $Tx2_i$.

Figure 19:
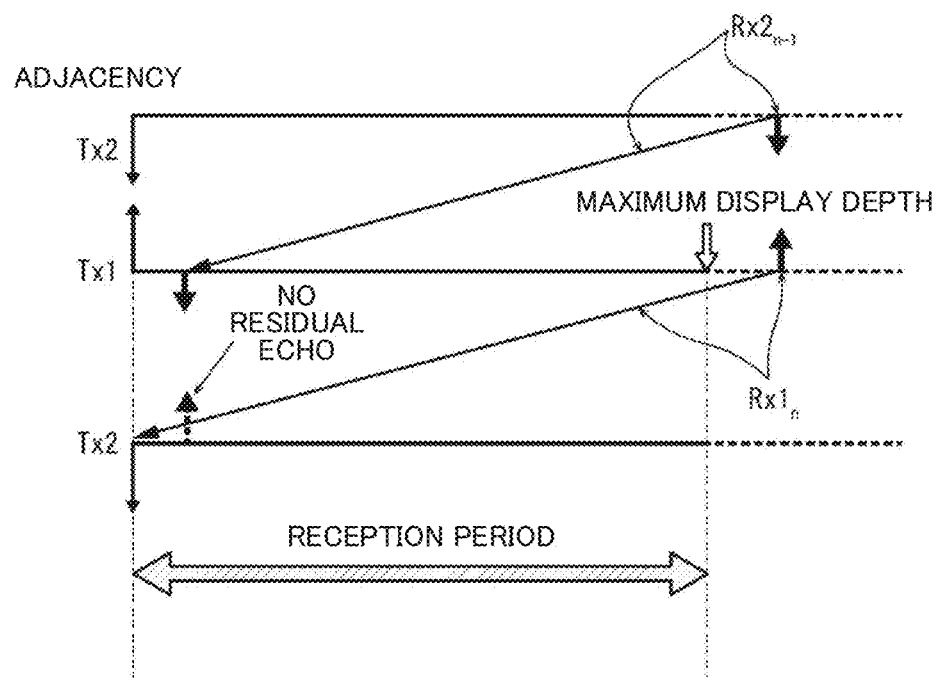
FIG. 19 is a schematic illustration of the way the reflected based on a transmitted ultrasound beam reaches a transducer in the ultrasound diagnostic device.

As illustrated in FIG. 19, by ensuring a sufficient time interval between the transmit waves Tx1 and Tx2 that constitute a set transmission for the same scan line, it is possible to prevent coupling of the reflected wave $Rx1_n$ from the deep highly reflective tissue based on the earlier transmit wave $Tx1_n$ into the reception result of the later transmit wave $Tx2_n$ performed for the same scan line (scan line number n). Thus, it can be prevented that the reflected wave $Rx1_n$ is detected as residual echo and, thus, is displayed in the display region as an artifact AR.

Figure 18:
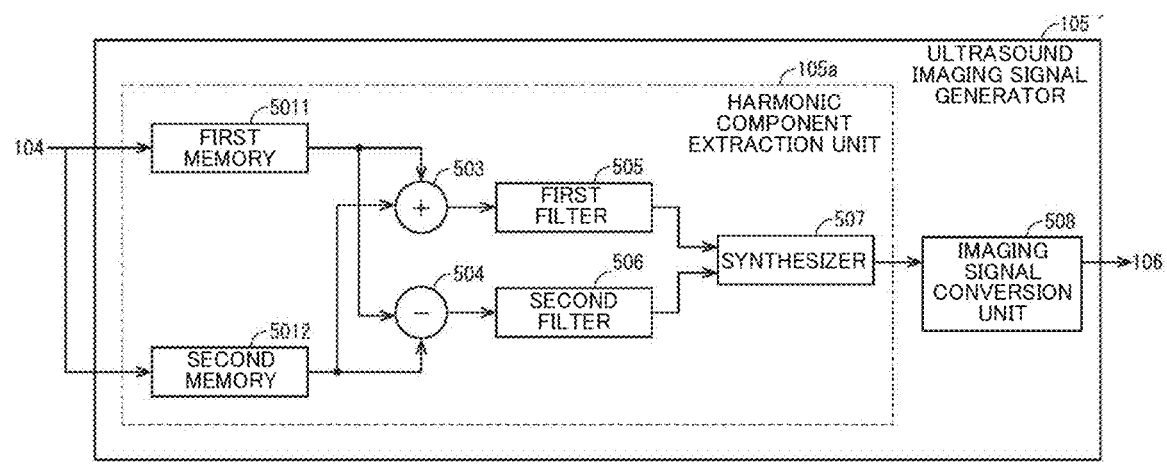
FIG. 18 is a functional block diagram illustrating the configuration of an imaging signal generator of the ultrasound diagnostic device according to the second embodiment.

FIG. 18 is a functional block diagram illustrating the configuration of imaging signal generator 105' of the ultrasound diagnostic device according to the second embodiment.

As described above, the ultrasound diagnostic device according to the second embodiment has a configuration in which transmission and reception regarding the transmit waves Tx1 and Tx2 constituting the set transmissions for the scan line numbers 1 to 192 are performed sequentially and alternately in accordance with the transmission order L. Therefore, it is required to have only first memory 5011 and second memory 5012 that store the line data of the first acoustic line signal and the line data of the second acoustic line signal for the same scan line in order to supply the line data to adder 503 or subtractor 504. As compared with the circuit configuration of ultrasound diagnostic device 100 according to the first embodiment illustrated in FIG. 9, third memory 5013 can be removed and, thus, the circuit configuration can be simplified.

Brief Summary

As described above, according to the ultrasound diagnostic device according to the second embodiment, in a low-cost device that does not require complicated control, by setting the time interval T1 between the transmit waves $Tx1_i$ and $Tx2_i$ which constitute a set transmission for at least the same scan line i, to a sufficient length of time, coupling of residual echo in the reception result of the subsequent transmit wave $Tx2_i$ can be prevented. As a result, it can be prevented that residual echo is displayed as an artifact.

Third Embodiment

Overview

The ultrasound signal processing method according to the third embodiment is a method in which the occurrence of coupling of residual echo is determined on the basis of a received information comparison result between rates, with the multiple-rate transmission and reception intervals being unequal. For example, in the case of the pulse inversion method, which is a typical example of an image formation method using multiple-rate transmission and reception, although the received echoes of the transmit wave Tx1 and the transmit wave Tx2 have inverted polarities and have waveform deformation due to the mon-linear effect, the echo intensities, that is, time-series amplitude information based on the envelope, have a certain degree of a correlation. For this reason, it does not happen that the echo intensity for the same tissue has a high amplitude in the transmit wave Tx1 but significantly low amplitude in the transmit wave Tx2 as compared with in the transmit wave Tx1. By setting the transmission intervals of transmit waves Tx1 and Tx2 to different values, the position at which residual echo enter (the depth directions) can be made different, and coupling of residual echo can be determined by detecting a decrease in the correlation coefficient of the amplitude information between the transmit waves Tx1 and Tx2 caused by residual echo.

Like the second embodiment, in the ultrasound diagnostic device according to the third embodiment, the transmit waves Tx1 and Tx2, which constitute a set transmission, are transmitted sequentially and alternately at different time intervals.

However, unlike the second embodiment, in the ultrasound diagnostic device according to the third embodiment, the time interval T1 between the transmit waves $Tx1_i$ and $Tx2_i$ that constitute a set transmission for the same scan line i is the time interval between the transmit wave $Tx1_i$ and the time the reflected wave $Rx1_i$ from the deep highly reflective tissue based on the earlier transmit wave $Tx1_i$ reaches the transducer during the reception period for the later transmit wave $Tx2_i$.

In addition, a signal part based on residual echo is detected on the basis of the line data of the first acoustic line signal and the line data of the second acoustic line signal acquired for the same scan line.

When residual echo is detected through the determination, the following first method is employed. That is, in the first method, the imaging signal for the part for which residual echo virtual image is detected is generated using the received signal based on only one of the transmit wave Tx1 and the transmit wave Tx2, instead of using the received calculation results obtained from calculation for the multiple rate transmissions.

The configuration of the ultrasound diagnostic device according to the third embodiment is described below.

Configuration

The ultrasound diagnostic device according to the third embodiment has a configuration in which the transmission sequence of the ultrasound beam transmitted by transmitter 103 based on the transmission control signal from controller 109 and ultrasound signal processing device 150 differ from those of the first and second embodiments. Accordingly, the details of the transmission sequence sent from controller 109 and the configuration and functions of ultrasound signal processing device 150 are mainly described with reference to the functional block diagram illustrating the configuration of the ultrasound diagnostic device. Since the other configurations are the same as those of the first embodiment, descriptions of the configurations are not repeated.

Transmission Sequence

FIG. 20 illustrates the transmission sequence at transmitter 103 of the ultrasound diagnostic device according to the third embodiment.

In FIG. 20, the meanings of transmission order L, scan line number i, and transmit wave type q are the same as in FIG. 16. Let transmit waves $Tx1_i$ and $Tx2_i$ denote a pair of transmit waves that constitute a set transmission for scan line number i and have a common transmission line. Then, the transmit waves $Tx1_i$ and $Tx2_i$ connected by the symbol "+" are transmitted in a set transmission by the pulse inversion method. More specifically, as illustrated in FIG. 20, according to the transmission order L (L=1 to 385), the transmit waves Tx1 and Tx2, which constitute the set transmissions for scan line number 1 to 192 and have a common transmission line, are transmitted sequentially and alternately. At this time, the ultrasound diagnostic device according to the third embodiment is characterized in that a time interval T1 between the transmit waves $Tx1_i$ and $Tx2_i$ in the set transmission of scan line number i differ from a time interval T2 between the transmit wave $Tx2_i$ in the set transmission for scan line number i and the transmit wave $Tx1_{i+1}$ in the set transmission for scan line number i+1. Note that the time interval T1 between the transmissions of transmit waves $Tx1_i$ and $Tx2_i$ for the same scan line may be the time interval between the transmissions of transmit waves $Tx1_i$ and the time the reflected wave $Rx1_i$ from the deep highly reflective tissue based on the earlier transmit wave $Tx1_i$ reaches the transducer during the reception period for the later transmit wave $Tx2_i$. Similarly, the time interval T2 between transmissions of the transmit waves $Tx1_i$ and $Tx2_i$ for the adjacent scan line may be the time interval between the transmit waves $Tx1_i$ and the time the reflected wave $Rx2_i$ from the deep highly reflective tissue based on the first transmit wave $Tx2_i$ reaches the transducer in the reception period for the second transmit wave $Tx1_{i+1}$. The ultrasound diagnostic device according to the third embodiment can prevent overlapping of residual echo coupled in the line data of the first acoustic line signal and residual echo coupled in the line data of the second acoustic line signal obtained for the same scan line on the basis of the difference between the time interval T1 and the time interval T2. Thus, the ultrasound diagnostic device can detect signal parts based on the residual echoes coupled in the line data of the first acoustic line signal and the second acoustic line signal.

Figure 21:
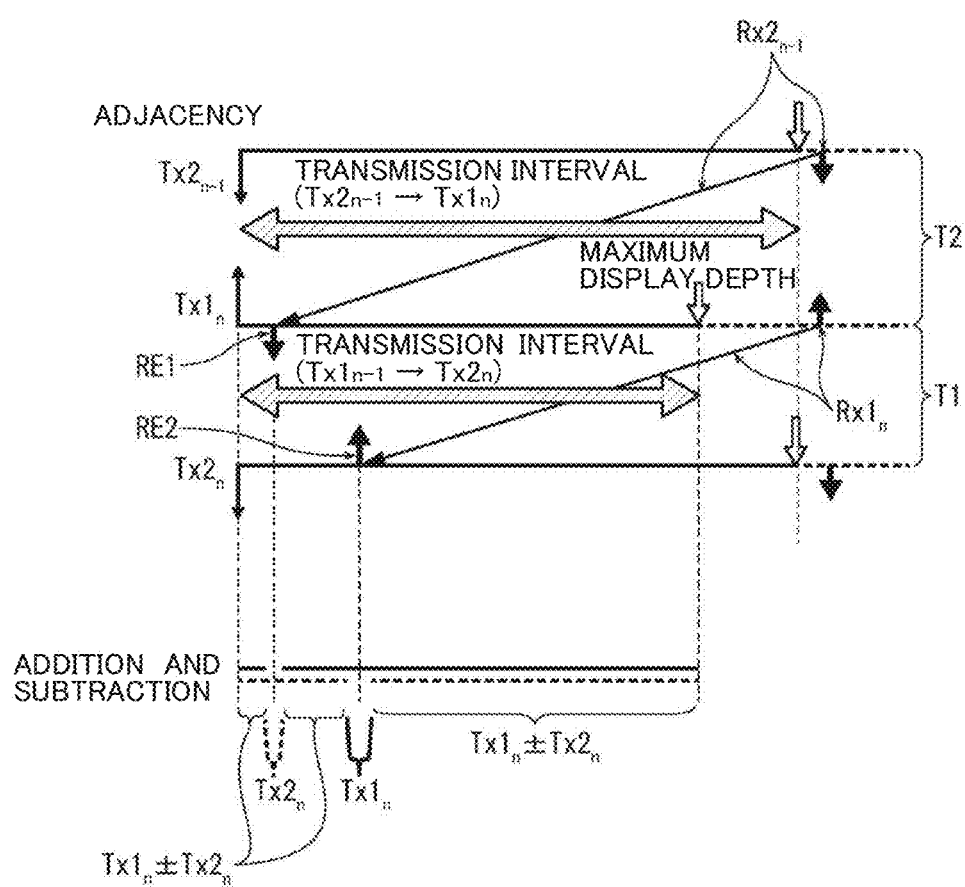
FIG. 21 is a schematic illustration of the way the reflected wave based on an ultrasound beam transmitted by the ultrasound diagnostic device reaches the transducer, according to the third embodiment.

FIG. 21 is a schematic illustration of the way the reflected wave based on the ultrasound beam transmitted by the ultrasound diagnostic device reaches the transducer, according to the third embodiment.

As described above, in the ultrasound diagnostic device according to the third embodiment, the transmit waves Tx1 and Tx2, which constitute the set transmission of the pulse inversion method, are sequentially and alternately transmitted at alternate different time intervals (Tx1 to Tx2, Tx2 to Tx1). Therefore, as illustrated in FIG. 21, the time required for the reflected wave $Rx1_n$ from the deep highly reflective tissue based on the earlier transmit wave $Tx1_n$ for the scan line n to reach the transducer within the reception period for the second transmit wave $Tx2_n$ differs from the time required for the reflected wave $Rx2_n$ from the deep highly reflective tissue based on the later transmit wave $Tx2_{n-1}$ for the immediately preceding scan line n−1 to reach the transducer within the reception period for the first transmit wave $Tx1_n$. As a result, the position of the virtual image signal part based on the residual echo coupled in the second acoustic line signal line data differs from the position of the virtual image signal part coupled in the first acoustic line signal line data. Thus, the configuration is employed in which the position of the virtual image signal part in the first acoustic line signal line data differs from that in the second acoustic line signal line data.

Ultrasound Imaging Signal Generator

In ultrasound imaging signal generator 105A (hereinafter also referred to as an "imaging signal generator 105A"), harmonic component extraction unit 105Aa has a configuration to detect a virtual image signal part based on residual echo by detecting and discriminating the significant abnormal signal part of the line data of the first acoustic line signal from the significant abnormal signal part in the line data of the second acoustic line signal acquired for the same scan line.

Figure 22:
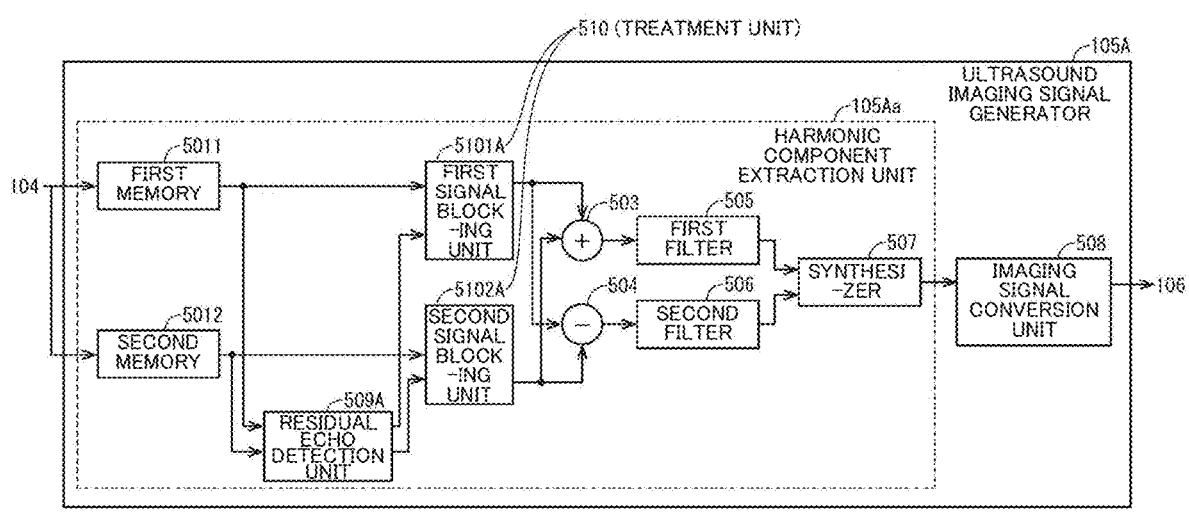
FIG. 22 is a functional block diagram illustrating the configuration of the imaging signal generator of the ultrasound diagnostic device according to the third embodiment.

FIG. 22 is a functional block diagram illustrating the configuration of imaging signal generator 105A of the ultrasound diagnostic device according to the third embodiment. As illustrated in FIG. 22, in imaging signal generator 105A, first memory 5011, second memory 5012, adder 503, subtractor 504, first filter 505, second filter 506, synthesizer 507, and imaging signal conversion unit 508 of harmonic component extraction unit 105Aa are the same as those of imaging signal generator 105 of the ultrasound diagnostic device according to the second embodiment illustrated in FIG. 18. Accordingly, the same reference numerals are used for the constituent elements, and description of the constituent elements are not repeated.

Unlike imaging signal generator 105, imaging signal generator 105A includes harmonic component extraction unit 105Aa equipped with treatment unit 510A including residual echo detection unit 509A, first signal blocking unit 5101A, and second signal blocking unit 5102A. The configurations of the units are described below.

First, in harmonic component extraction unit 105Aa illustrated in FIG. 22, the line data of the first acoustic line signal and the line data of the second acoustic line signal output from receiver 104 are stored in first memory 5011 and second memory 5012, respectively, in accordance with the transmission order L.

Residual echo detection unit 509A reads the line data of the first acoustic line signal and the line data of the second acoustic line signal from first memory 5011 and second memory 5012, respectively, performs cross-correlation processing on the line data of the first acoustic line signal and the line data of the second acoustic line signal, and detects, as a virtual image signal part, the part where the significant signal with a low correlation degree exists. That is, residual echo detection unit 509A compares the line data of the first acoustic line signal with the line data of the second acoustic line signal. Thereafter, residual echo detection unit 509A outputs, to first signal blocking unit 5101A, information about the position of a signal part of the line data of the first acoustic line signal that is not present in the line data of the second acoustic line signal. In addition, residual echo detection unit 509A outputs, to second signal blocking unit 5102A, information about the position of a signal part of the line data of the second acoustic line signal that is not present in the line data of the first acoustic line signal.

First signal blocking unit 5101A acquires the line data of the first acoustic line signal from first memory 5011 and acquires the information about the position of the virtual image signal part in the line data of the first acoustic line signal from residual echo detection unit 509A. Thereafter, first signal blocking unit 5101A deletes the signal part from which the virtual image signal part is detected and outputs the first acoustic line signal to adder 503 and subtractor 504.

When determining which one of the received information about the transmit wave Tx1 and the transmit wave Tx2 is used, the received information that exhibits a small amplitude when the correlation coefficient between the received information of the transmit wave Tx1 and the received information of the transmit wave Tx2 decreases. In this manner, the received information without coupled residual echo can be obtained.

Although two types of received information, one based on the result of reception calculation and the other obtained without calculation, are present in one imaging signal, the usefulness of being able to remove the residual echo virtual image and display the correct echo level is more important. This is because a problem prominently arises when residual echo virtual image appears in a no-echo region or a low echo region and, therefore, even when the quality of the received information changes, the loss of information is small, since the received information is originally small.

Similarly, second signal blocking unit 5102A acquires the line data of the first acoustic line signal from second memory 5012 and acquires the information about the position of the virtual image signal part in the line data of the second acoustic line signal from residual echo detection unit 509A. Thereafter, second signal blocking unit 5102A deletes the signal part from which a virtual image signal part is detected and outputs the second acoustic line signal to adder 503 and subtractor 504.

Adder 503 reads, from first signal blocking unit 5101A, the line data of the first acoustic line signal with the virtual image signal part removed, reads, from second signal blocking unit 5102A, the line data of the second acoustic line signal with the virtual image signal part removed, sums the two line data to extract the even-order harmonic component. Adder 503 outputs the even-order harmonic component to first filter 505.

At this time, since the virtual image signal part of the line data of one of the first acoustic line signal and the second acoustic line signal is deleted, the addition process is not performed on the signal part. For this reason, the even-order harmonic component cannot be extracted. Therefore, for the signal part from which the virtual image signal is detected, only the fundamental harmonic component of the line data of the other acoustic line signal, for which a virtual image signal part is not detected, is output to first filter 505.

Similarly, subtractor 504, which is used as needed, reads, from first signal blocking unit 5101A, the line data of the first acoustic line signal with the virtual image signal part removed, reads, from second signal blocking unit 5102A, the line data of the second acoustic line signal with the virtual image signal part removed. Thereafter, subtractor 504 subtracts the line data of the second acoustic line signal from the line data of the first acoustic line signal, extracts the fundamental harmonic component and the odd-order harmonic component, and outputs the fundamental harmonic component and the odd-order harmonic component to second filter 506.

At this time, since the virtual image signal part of the line data of one of the first acoustic line signal and the second acoustic line signal has been deleted, the subtraction process is not performed on the signal part and, therefore, the odd-order harmonic component cannot be extracted. For this reason, for the signal part in which the virtual image signal is detected, only the fundamental harmonic component of the line data of the other acoustic line signal from which a virtual image signal part is not detected is output to second filter 506.

Subsequently, synthesizer 507 and imaging signal conversion unit 508 generate the ultrasound imaging signal line data and the like, which are output to imaging signal synthesizer 106. In this way, the virtual image signal part caused by residual echo are removed from each of the first acoustic line signal and the second acoustic line signal, and the imaging signal line data is generated. In this manner, an artifact in the displayed image can be reduced.

Particular Example of Method for Detecting Coupling of Residual Echo

A particular example of a third method according to the present invention is described below. In the third method, the transmission and reception intervals of the multiple rate transmission and reception are not the same, and the occurrence of coupling of residual echo is determined on the basis of the comparison results of the received information between the multiple rates.

For example, in the case of pulse inversion, one of the following methods is used to compare received information between multiple rates: (1) reversing the polarity of one reception time waveform information piece and, thereafter, comparing two reception time waveform information pieces, (2) performing a convolution operation with a template prepared in advance and comparing the results of the operations, (3) performing Fourier transformation on the time waveform information over a certain interval and comparing the frequency components, and (4) obtaining the envelopes of the received time waveform information and comparing the envelopes. In any one of the above methods, it is desirable to perform processing so that the time intervals are averaged enough to absorb differences in the direction of waveform deformation due to nonlinear effects.

Figure 23A:
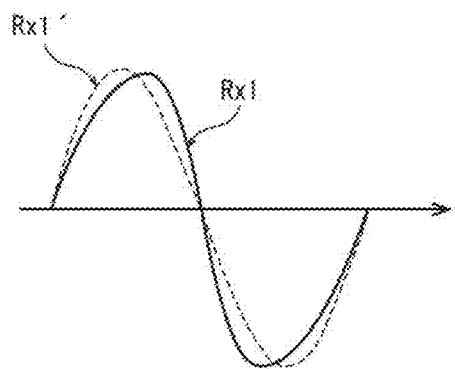
FIG. 23A is a schematic illustration of part of a time averaging process performed by residual echo detection unit of the ultrasound diagnostic device according to the third embodiment.
Figure 23B:
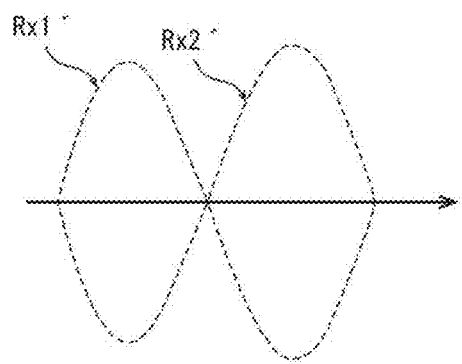
FIG. 23B is a schematic illustration of part of the time averaging process performed by the residual echo detection unit of the ultrasound diagnostic device according to the third embodiment.

That is, after performing a time averaging process, residual echo detection unit 509A may perform cross-correlation processing on the line data of the input first acoustic line signal and the line data of the input second acoustic line signal to detect the virtual image signal part. FIGS. 23A and 23B are schematic illustrations of part of the time averaging process performed by the residual echo detection unit of the ultrasound diagnostic device according to the third embodiment.

As illustrated in FIG. 23A, line data Rx1 of the first acoustic line signal and line data Rx2 of the second acoustic line signal input to residual echo detection unit 509A have different directions of waveform deformation due to nonlinear effects. For this reason, a high correlation cannot be obtained through simple inversion comparison. Therefore, it is desirable to generate received signals Rx1' and Rx2' subjected to a process of averaging time intervals sufficient to absorb the difference in the deformation direction and, thereafter, compare the received signal Rx1' with the received signal Rx2'. At this time, the time average may be a time average for one or more wavelengths of the lowest probe band frequency. For example, if the lowest probe band frequency is 4 to 18 MHz, the time averaging may be performed over one wavelength at 4 MHz.

In addition, in the methods listed above, it is desirable that residual echo detection unit 509A compare the first acoustic line signal and the second acoustic line signal using information on the basis of the envelope. For example, it is desirable to compare the two acoustic line signals after applying envelope detection, in order to reduce the processing load and the number of comparison data points.

Furthermore, the comparison may be made after a thinning process within a range in which the number of data points is not less than the number of pixels at the time of image display. The comparison determination process is preferably a determination process based on the correlation coefficients, and the threshold for residual echo determination is appropriately set and selected (including user selection) in consideration of the shape of the probe, scanning method (linear type, sector type, etc.), probe frequency band, transmission/reception frequency, display depth, observation area, and the like.

Operation

The harmonic component extraction process performed by the ultrasound diagnostic device having the configuration according to the third embodiment is described below.

Figure 24:
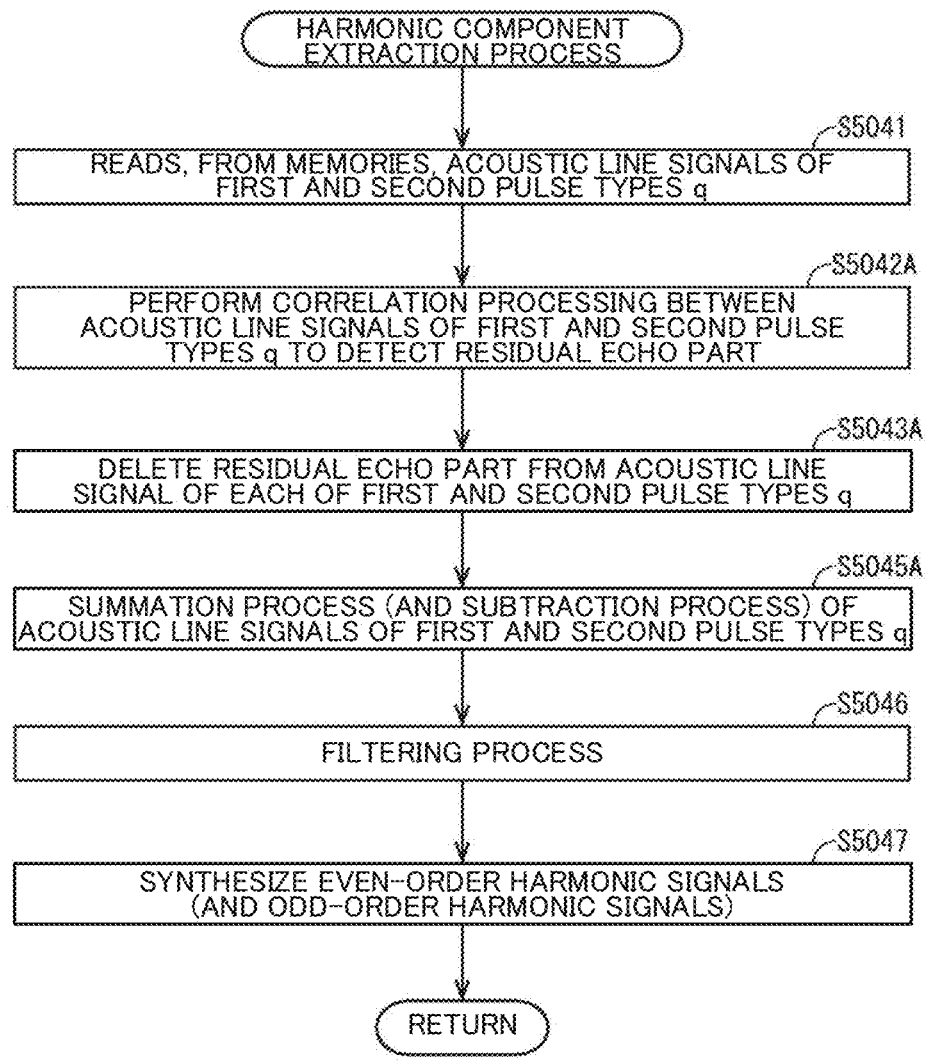
FIG. 24 is a flowchart illustrating the details of a harmonic component extraction process (step S504 in FIG. 12) performed by the ultrasound diagnostic device according to the third embodiment.

FIG. 24 is a flowchart illustrating the details of the harmonic component extraction process (step S504 in FIG. 12) performed by the ultrasound diagnostic device according to the third embodiment.

Harmonic component extraction unit 105Aa reads the first acoustic line signal line data and the second acoustic line related to the first and second pulse types q for the same scanning line Bxi from first memory 5011 and second memory 5012, respectively (step S5041), performs correlation processing between the first and second acoustic line signal line data to detect the position of the virtual image signal part based on the residual echo (step S5042A), and deletes the virtual image signal parts based on the residual echo from the first and second acoustic line signal line data (step S5043A). Thereafter, by performing an addition process on the first and second acoustic signal line data from which the virtual image signal part has been removed by adder 503, harmonic component extraction unit 105Aa extracts the even-order harmonic component from the signal part other than the virtual image part. In addition, by performing a subtraction process by subtractor 504 as needed, harmonic component extraction unit 105Aa extracts the odd-order harmonic component from the signal part other than the virtual image part (step S5045A). Subsequently, harmonic component extraction unit 105Aa removes the fundamental harmonic component from the subtraction result through the filtering process (step S5046) to extract only the odd-order harmonic components, synthesizes an even-order harmonic signal and the odd-order harmonic signal, which is extracted as needed (step S5047), generates the line data of the acoustic line signal including the harmonic components, and outputs the line data to imaging signal conversion unit 508.

Brief Summary

As described above, the ultrasound diagnostic device according to the third embodiment prevents overlapping of residual echoes that occur when the reflected wave $Rx1_n$ from the deep highly reflective tissue based on one of the transmit waves Tx1 and Tx2 is coupled in when receiving the other transmit wave. As a result, the ultrasound diagnostic device can detect a virtual image signal part caused by the residual echo coupled in each of the first acoustic line signal and second acoustic line signal, independently. Thereafter, the ultrasound diagnostic device can remove the virtual image signal part caused by the residual echo from each of the first acoustic line signal and second acoustic line signal and display an image.

At this time, since the virtual image signal parts are independently detected and removed on the basis of the received signal of the transmit wave Tx1 or Tx2 for the same scan line, degradation of the resolution in the azimuth direction can be prevented.

In addition, the ultrasound diagnostic device according to the third embodiment can perform the process of detecting and removing a virtual image signal part caused by residual echo in a significantly short time, as compared with the technology described in Japanese Patent Application Laid-Open No. 2007-244501 in which frame data for two screens is generated and the frame subtraction method is performed. Thus, the ultrasound diagnostic device can perform the process on a line data-by-line data basis in the moving image display process.

More specifically, according to the method in which the image difference between frames is detected by changing the transmission interval on a frame-by-frame basis requires the transmission-reception time corresponding to the number of transmissions that form one frame (for example, 192 transmissions if one frame consists of 192 scan lines). Determination is influenced by movement such as a probe operation and, thus, erroneous determination often occurs. In contrast, according to the method of the third embodiment, in the above-described example, only 1/192 of the time is required and, thus, erroneous determination rarely occurs.

Therefore, it can be prevented that residual echo is displayed in the display region as the artifact AR, without reducing the frame rate in displaying a moving image.

The above-described technique is only an example, and residual echo virtual images may be reduced by other imaging signal formation methods.

Second Modification

An ultrasound diagnostic device according to the second modification may have a configuration in which virtual image signal parts caused by residual echoes coupled in the first acoustic line signal and second acoustic line signal are detected and, thereafter, one of different operations may be adaptively performed. When residual echo is detected by determination, the detection result can be used in a variety of ways.

For example, if a virtual image signal part based on residual echo is detected, a warning message indicating that an artifact due to the residual echo is displayed in the display region may be displayed when a moving image is displayed. In this case, the moving image may be still displayed together with a warning message indicating that residual echo has been detected.

Alternatively, for example, when an image portion based on the acoustic line signal in which residual echo was detected is displayed, the part corresponding to an artifact may be colored to contrast with the other part. In this case, the part in which residual echo was not detected is displayed in a normal black and white image, whereas the prat in which residual echo was detected is colored and displayed so as to be distinguished from the part in which residual echo was not detected.

Alternatively, by increasing the transmission intervals of both transmit waves Tx2 and Tx2 for the frames subsequent to the frame in which residual echo is detected, the pulse repetition frequency is reduced and, thus, a virtual image due to residual echo is no longer displayed in the subsequent frames, although a virtual image is displayed in the current frame. Still alternatively, if an artifact is detected, the pulse repetition frequency in subsequent transmission-receptions may be reduced.

Yet still alternatively, if residual echo is detected, transmission for the subsequent scan line may be stopped and, immediately thereafter, retransmission with an increased transmission interval between the transmit waves Tx1 and Tx2 may be performed for the same scan line so that an image containing residual echo virtual image is not displayed in the current frame and the subsequent frames. In this case, by performing again a set transmission with the pulse period being increased for the same scan line for which an artifact was detected, imaging signal line data with a reduced artifact due to residual echo may be generated. Thereafter, the pulse period may be changed back to the prior pulse period, and the set transmission may be repeated.

As described above, an artifact in a displayed image can be reduced.

Third Modification

Overview

The ultrasound diagnostic device according to the third embodiment has a configuration in which transmit waves Tx1 and Tx2, which constitute a set transmission of a pulse inversion method, are transmitted sequentially and alternately at alternate different time intervals (Tx1 to Tx2, Tx2 to Tx1) so as to detect virtual image signal parts caused by residual echoes coupled in the first and second acoustic line signals, and the virtual image signal parts caused by residual echoes are removed from the first and second acoustic line signals and are displayed. In the ultrasound diagnostic device according to the third embodiment, it is possible to determine coupling of residual echo by detecting residual echo-induced decrease in the correlation coefficient between the amplitude information pieces about the acoustic line signals based on the transmit waves Tx1 and Tx2.

According to the third modification, as a second method for forming an imaging signal from the obtained acoustic line signal when residual echo is detected by the determination, the ultrasound diagnostic device has a configuration in which the transmit waves Tx1 and Tx2, which constitute the set transmission in the pulse inversion method, are transmitted at unequal intervals and, in addition, the transmission order of the transmit waves Tx1 and Tx2 is alternated from set transmission to set transmission. Furthermore, the imaging signal line data may be generated by replacing the virtual image signal part of the acoustic line signal line data with the corresponding signal part of acoustic line signal line data of the same polarity in the past than the acoustic line signal line data.

That is, the transmission order of the transmit waves Tx1 and Tx2 is switched in the adjacent scan lines, and the received information of the transmit waves Tx1 and Tx2 in the adjacent scan lines is used to obtain the reception calculation results only in the area where no residual echoes are coupled. Although the quality of the received information in the azimuthal direction changes because the calculation is performed with the adjacent scan line, this method is a particularly useful in the following case. That is, in a simultaneous display mode, which is a combination of B-mode and one of color mode and M-mode, instead of B-mode alone, the operator's attention is often focused on a display area in a mode other than B-mode. Thus, displaying of residual echo virtual image does not interfere with the operator's attention and observation.

The configuration of the ultrasound diagnostic device according to the third modification is described below.
Configuration The ultrasound diagnostic device according to the third modification has a configuration in which the transmission sequence of the ultrasound beam at transmitter 103 based on the transmission control signal from controller 109 and ultrasound signal processing device 150B differ from those according to the third embodiment. Accordingly, the configuration and functions of the transmission sequence sent from controller 109 and ultrasound signal processing device 150B are mainly described with reference to the functional block diagram illustrating the configuration of the ultrasound diagnostic device. Since the other configurations are the same as those of the first embodiment, descriptions of the configurations are not repeated.
Transmission Sequence FIG. 25 illustrates the transmission sequence at transmitter 103 of the ultrasound diagnostic device according to the third modification.

In FIG. 25, the meanings of the transmission order L, scan line number i, transmit wave type q, and symbol "+" are the same as in FIG. 10. More specifically, as illustrated in FIG. 25, the configuration is employed in which set transmission is repeated for scan line numbers 1 to 192 in accordance with the transmission order L (L=1 to 385) such that the transmission orders of transmit waves Tx1 and Tx2 with different polarities are reversed from set transmission to set transmission. In addition, like the ultrasound diagnostic device according to the third embodiment, the time interval T1 between the transmit waves $Tx1_i$ and $Tx2_i$ in the set transmission of scan line number i differs from the time interval T2 between the transmit wave $Tx1_i$ or $Tx2_i$ in the set transmission for scan line number i and the transmit wave $Tx1_{i+1}$ or $Tx2_{i+1}$ in the set transmission for scan line number i+1. Note that each of the time intervals T1 and T2 of the transmissions is the time interval between transmission of the earlier transmit wave and the time the reflected wave from the deep highly reflective tissue based on the earlier transmit wave reaches the transducer during the reception period for the later transmit wave.

Figure 26:
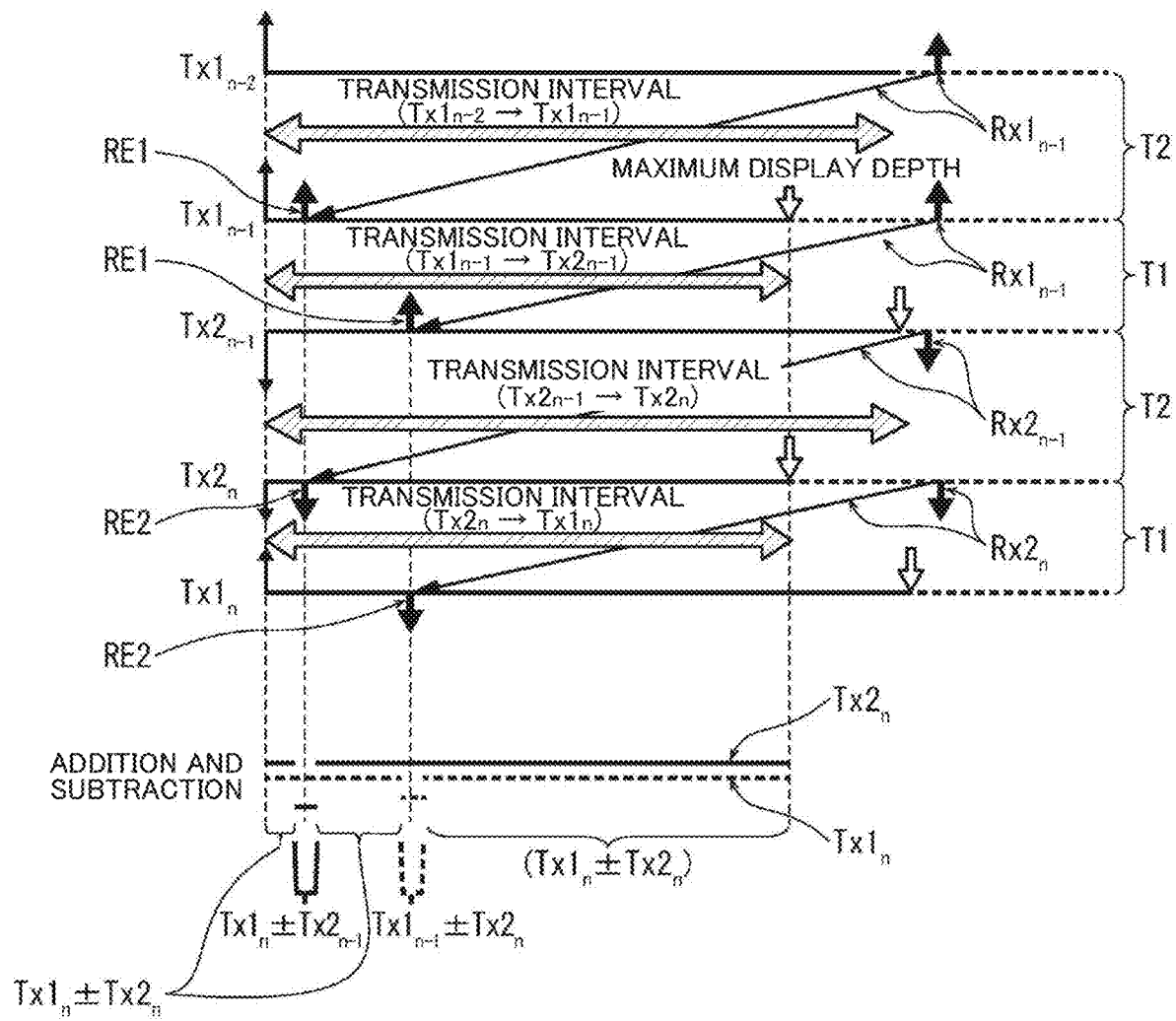
FIG. 26 is a schematic illustration of the way the reflected wave based on an ultrasound beam transmitted by the ultrasound diagnostic device reaches a transducer, according to the third modification.

FIG. 26 is a schematic illustration of the way the reflected wave of the ultrasound beam transmitted by the ultrasound diagnostic device according to the third modification reaches the transducer.

Figure 27:
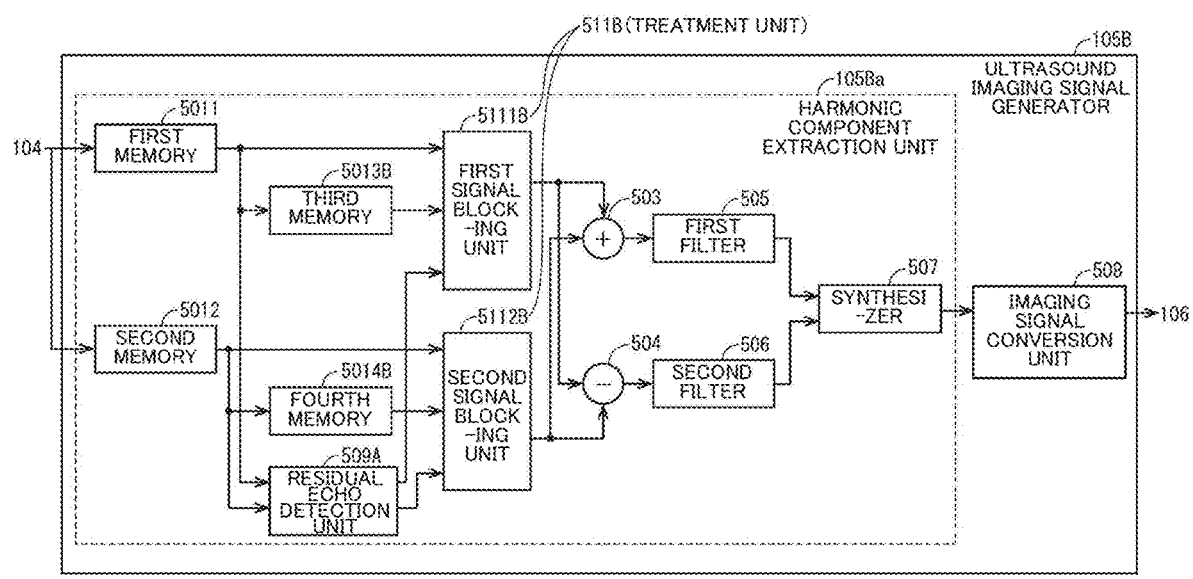
FIG. 27 is a functional block diagram illustrating the configuration of an imaging signal generator of the ultrasound diagnostic device according to the third modification.

As described above, like the ultrasound diagnostic device according to the third embodiment, in the ultrasound diagnostic device according to the third modification, the transmit waves Tx1 and Tx2, which constitute the set transmission of the pulse inversion method, are transmitted at alternate different time intervals (Tx1 to Tx2, Tx2 to Tx1). This prevents overlapping of residual echoes RE1 and RE2 when the reflected wave Rx1 or Rx2 from the deep highly reflective tissue based on one of the transmit waves Tx1 and Tx2 is coupled in during reception of the other of transmit waves Tx1 and Tx2. The virtual image signal parts due to the residual echoes coupled in the first acoustic line signal and the second acoustic line signal can be detected independently.
Ultrasound Imaging Signal Generator FIG. 27 is a functional block diagram illustrating the configuration of ultrasound imaging signal generator 105B (hereinafter referred to as "imaging signal generator 105B") of the ultrasound diagnostic device according to the third modification. As illustrated in FIG. 27, in imaging signal generator 105B, the configurations of first memory 5011, second memory 5012, adder 503, subtractor 504, first filter 505, second filter 506, synthesizer 507, imaging signal conversion unit 508, and residual echo detecting unit 509A in harmonic component extraction unit 105Ba are the same as those in imaging signal generator 105A of the ultrasound diagnostic device according to the second embodiment illustrated in FIG. 22. Accordingly, the same reference numerals are used for the constituent elements, and description of the constituent elements are not repeated.

Unlike imaging signal generator 105A, imaging signal generator 105B includes harmonic component extraction unit 105Ba equipped with treatment unit 511B including first signal blocking unit 5111B and second signal blocking unit 5112B. The configurations of the constituent elements are described below.

Like harmonic component extraction unit 105Aa, in harmonic component extraction unit 105Ba illustrated in FIG. 22, the line data of the first acoustic line signal and the line data of the second acoustic line signal output from receiver 104 are stored in first memory 5011 and second memory 5012, respectively, in accordance with the transmission order L. In addition, the line data of the first acoustic line signal and the line data of the second acoustic line signal stored in first memory 5011 and second memory 5012 are output to third memory 5013B and fourth memory 5014B and are stored therein, respectively, in synchronization with the output from imaging signal generator 105B to the subsequent stage. As a result, third memory 5013B and fourth memory 5014B store the line data of the first acoustic line signal and the line data of the second acoustic line signal regarding the set transmission immediately preceding the set transmission regarding those in first memory 5011 and second memory 5012, respectively, where the line data in third memory 5013B and the line data in first memory 5011 have the same polarity, and the line data in fourth memory 5014B and the line data in second memory 5012 have the same polarity.

Detection of the virtual image signal part performed by residual echo detection unit 509A is the same as that performed by imaging signal generator 105A.

First signal blocking unit 5111A acquires, from first memory 5011, the line data of the first acoustic line signal and acquires, from third memory 5013B, the line data of the first acoustic line signal having the same polarity regarding the immediately preceding set transmission (the signal is referred to as an "immediately preceding same-polarity acoustic line signal"). In addition, first signal blocking unit 5111A acquires, from residual echo detection unit 509A, the information about the position of the virtual image signal part in the line data of the first acoustic line signal. Thereafter, first signal blocking unit 5111A replaces the signal part of the line data of the first acoustic line signal from which the virtual image signal part is detected with the corresponding part of the immediately preceding same-polarity acoustic line signal. First signal blocking unit 5111A outputs the first acoustic line signal to adder 503 and subtractor 504.

Similarly, second signal blocking unit 5112A acquires, from second memory 5012, the line data of the second acoustic line signal and acquires, from fourth memory 5014B, the immediately preceding same-polarity acoustic line signal. In addition, second signal blocking unit 5112A acquires, from residual echo detection unit 509A, information about the position of the virtual image signal part in the line data of the second acoustic line signal. Thereafter, second signal blocking unit 5112A replaces the signal part of the line data of the second acoustic line signal from which the virtual image signal part is detected with the corresponding part of the immediately preceding same-polarity acoustic line signal. Second signal blocking unit 5112A outputs the second acoustic line signal to adder 503 and subtractor 504.

Adder 503 acquires, from first signal blocking unit 5111A, the line data of the first acoustic line signal in which the virtual image signal part is replaced with the corresponding part of the immediately preceding same-polarity acoustic line signal and acquires, from second signal blocking unit 5112A, the line data of the second acoustic line signal in which the virtual image signal part is replaced with the corresponding part of the immediately preceding same-polarity acoustic line signal and sums the two line data. Thus, adder 503 extracts the even-order harmonic component and outputs the even-order harmonic component to first filter 505.

At this time, the virtual image signal part in the line data of the first acoustic line signal or the line data of the second acoustic line signal is subjected to a summation process using the corresponding part of the immediately preceding same-polarity acoustic line signal to extract the even-order harmonic component. Therefore, unlike the third embodiment, even for the signal part from which a virtual image signal is detected, the even-order harmonic component based on the line data of the first acoustic line signal or the line data of the second acoustic line signal is extracted throughout the line and is output to first filter 505.

Similarly, subtractor 504, which is used as needed, acquires, from first signal blocking unit 5111A, the line data of the first acoustic line signal having the virtual image signal part replaced with the corresponding part of the immediately preceding same-polarity acoustic line signal and acquires, from second signal blocking unit 5112A, the line data of the second acoustic line signal having the virtual image signal part replaced with the corresponding part of the immediately preceding same-polarity acoustic line signal and subtracts the line data of the second acoustic line signal from the line data of the first acoustic line signal. Thus, subtractor 504 extracts the fundamental harmonic component and the odd-order harmonic component and output the fundamental harmonic component and the odd-order harmonic component to second filter 506.

At this time, the virtual image signal part in the line data of the first acoustic line signal or the line data of the second acoustic line signal is subjected to a summation process using the corresponding part of the immediately preceding same-polarity acoustic line signal to extract the even-order harmonic component. Therefore, unlike the third embodiment, the fundamental harmonic component and the odd-order harmonic components based on the line data of the first acoustic line signal or the line data of the second acoustic line signal are extracted throughout the line and are output to second filter 506.

Synthesizer 507 and imaging signal conversion unit 508 generate the line data of the ultrasound imaging signal and the like and outputs the line data and the like to imaging signal synthesizer 106.

Operation

The harmonic component extraction process performed by the ultrasound diagnostic device having the above-described configuration according to the third modification is described below.

Figure 28:
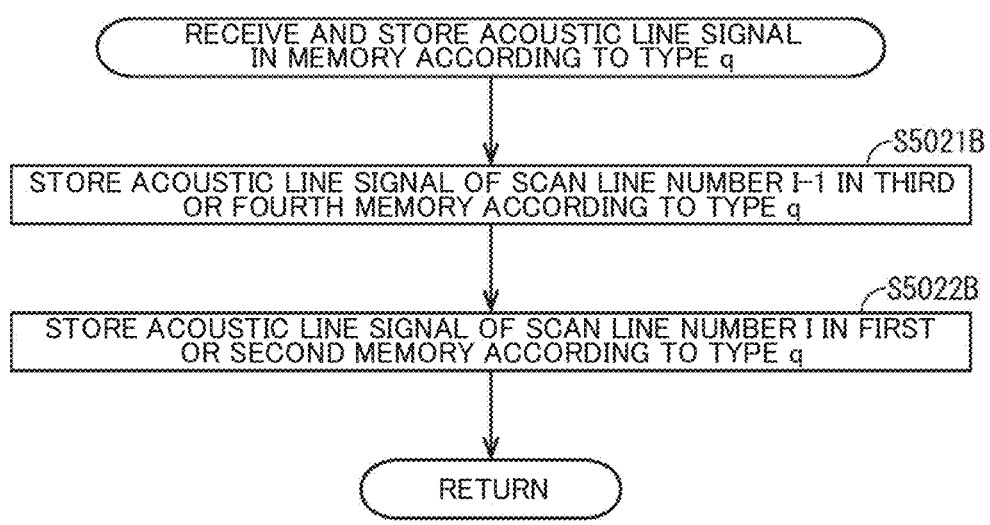
FIG. 28 is a flowchart illustrating the details of an acoustic line signal storing process (step S502 in FIG. 12) performed by the ultrasound diagnostic device according to the third modification.

FIG. 28 is a flowchart illustrating the details of an acoustic line signal storing process (step S502 in FIG. 12) performed by the ultrasound diagnostic device according to the third modification.

In the acoustic line signal storing process, the acoustic line signal of scan line number 1-1 is stored in third memory 5013B or fourth memory 5014B according to type q first (step S5021B). Subsequently, the acoustic line signal of scan line number I is received, and the acoustic line signal is stored in first memory 5011B or second memory 5012B according to type q (step S5022B).

Figure 29:
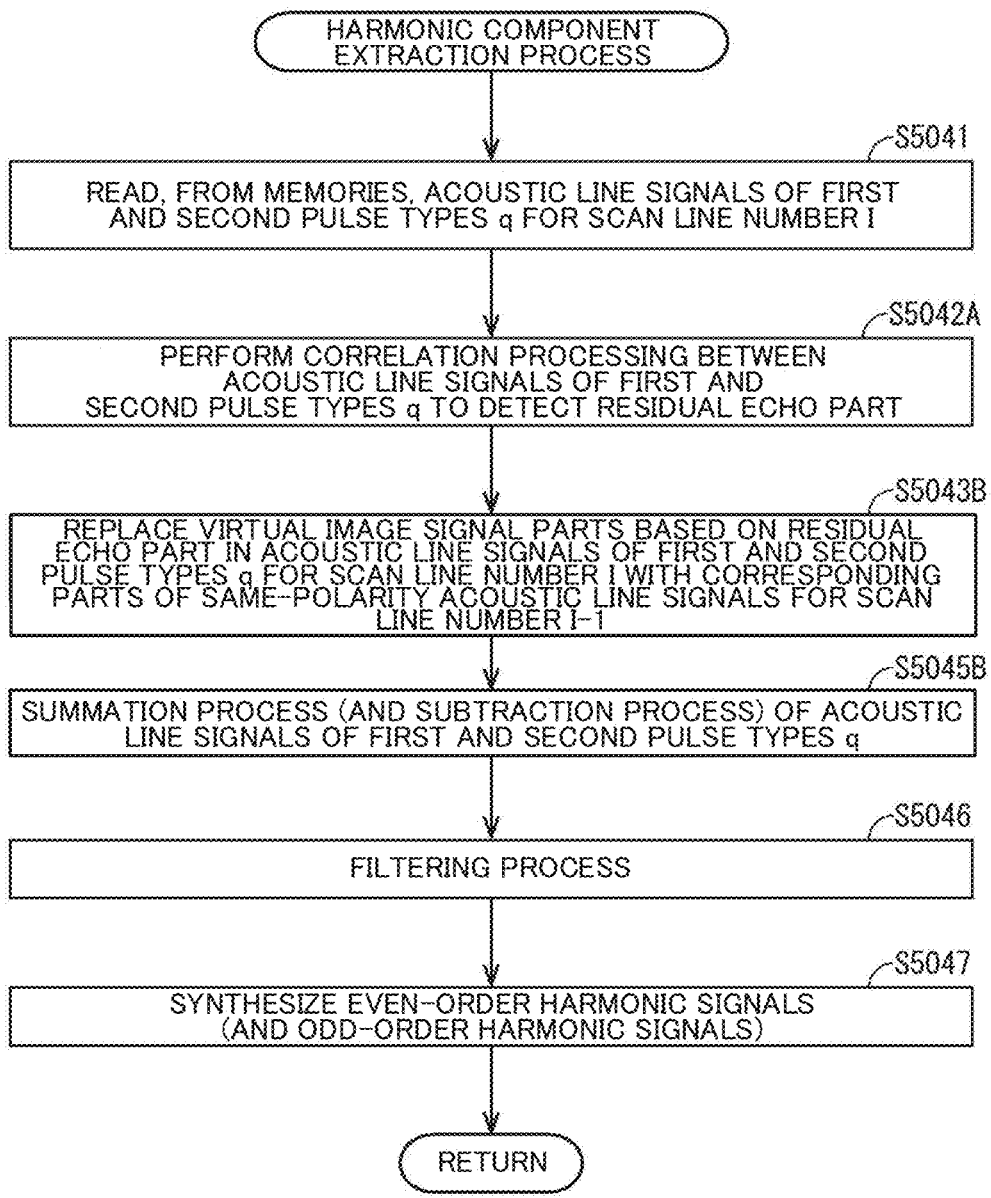
FIG. 29 is a flowchart illustrating the details of a harmonic component extraction process (step S504 in FIG. 12) performed by the ultrasound diagnostic device according to the third modification.

FIG. 29 is a flowchart illustrating the details of the harmonic component extraction process (step S504 in FIG. 12) performed by the ultrasound diagnostic device according to the third modification.

The process of receiving the acoustic line signal in step S5041 and the process of detecting the residual echo in step S5042A are the same as the processes performed by harmonic component extraction unit 105Aa illustrated in FIG. 24.

In step S5043B, the virtual image signal part based on residual echo in the acoustic line signals of the first and second pulse types q for scan line number I are replaced with the corresponding parts of the immediately preceding same-polarity acoustic line signals. Thereafter, the first and second acoustic line signal line data each having the virtual image signal part replaced with the corresponding part of the immediately preceding same-polarity acoustic line signal of the same polarity are summed by adder 503 to extract even-order harmonic component for the entire line including the virtual image signal part. In addition, a subtraction process is performed by subtractor 504 to extract odd-order harmonic component for the entire line including the virtual image signal part (step S5045B).

The filtering process in step S5046 and the synthesizing process in step S5047 are the same as the processes performed by harmonic component extraction unit 105Aa illustrated in FIG. 24. In the above-described manner, the line data of the acoustic line signal from which the harmonic components have been extracted is generated and output to imaging signal conversion unit 508.

Brief Summary

As described above, by preventing overlapping of residual echoes, the ultrasound diagnostic device according to the third modification can detect virtual image signal parts caused by coupled residual echoes independently and can generate the imaging signal line data from which a harmonic signal is extracted for the entire line by replacing the virtual image signal parts caused by residual echo in the first and second acoustic line signals with the corresponding parts of the acoustic line signals of the immediately preceding same-polarity acoustic line signals. In this manner, by using the harmonic signal of the immediately preceding same-polarity acoustic line signal for the part where the virtual image signal was detected, degradation of the distance resolution and contrast can be prevented. As a result, an artifact in the displayed image can be reduced more.

The above-described processing is only an example, and the occurrence of residual echo virtual image may be reduced by another method for forming an imaging signal.

Other Modifications (1) Multi-rate transmission and reception according to the present disclosure is not limited to a method for forming an imaging signal by calculating the results of two transmission/reception events, such as the phase inversion method (typically, the pulse inversion method) or the pulse amplitude modulation (PM) method. For example, a method for forming an imaging signal by calculating three or more transmission/reception results may be employed, such as the pulse inversion pulse amplitude modulation (PIPM) method that combines the phase inversion method and the pulse amplitude modulation method or a method for extracting the third harmonic by performing three transmissions in which the phase is shifted by 180 degrees for each transmission and calculating the results.

(2) The aspects of the present disclosure may be automatically or user-selectively applied in accordance with the display mode (B-mode, B-mode+color Doppler, B-mode and color Doppler+pulse Doppler, B-mode+ultrasound elasticity analysis, B-mode+contrast agent harmonic imaging). For example, when only a B mode image is displayed, the second aspect may be applied. In contrast, in the simultaneous display mode (B mode+color Doppler+pulsed Doppler) that requires a high frame rate, the frame rate may be of a higher priority than prevention of residual echo, so that the transmission interval between the transmit wave Tx1 and transmit wave Tx2 may be minimized to stop a reduction of residual echo. Alternatively, when the method according to the third embodiment of the present disclosure is applied to an ultrasound diagnostic device that does not have a high signal processing capability, residual echo determination may be made when only a B mode image is displayed. However, in the case of B mode+ultrasonic elastic analysis that increases the signal processing load, residual echo determination may not be made. In this manner, the aspect of the present disclosure may or may not be applied in consideration of the user's request and the priority of the processing load.

(3) In the ultrasound diagnostic device according to the above-described embodiment, the configurations of transmitter 103 and receiver 104 are not limited to those described in the embodiment and can be changed as appropriate. For example, in the ultrasound diagnostic device according to the above-described embodiment, the phasing addition unit performs the phasing addition process for a plurality of observation points located in each of the plurality of regions to be calculated to generate a plurality of line data of the acoustic line signal, and the imaging signal synthesizer synthesizes signals based on the generated frame data of the acoustic line signal on the basis of the positions of the observation points and generates frame data of the ultrasound imaging signal. In contrast, the ultrasound diagnostic device according to a modification may store signals acquired through a phasing addition process performed by the phasing addition unit for a plurality of regions to be calculated in a memory, such as image memory 106a, and generate frame data for one frame on the basis of the stored signals. That is, the ultrasound diagnostic device may have a configuration to generate the frame data of an ultrasound imaging signal without performing the process of generating the line data as a set of data corresponding to a plurality of regions to be calculated.

(4) Transmitter 103 may have a configuration to set a row Tx of the transmit transducers, which are a subset of a plurality of transducers 101a disposed in probe 101, repeat ultrasound transmission while gradually moving the row Tx of transmit transducers in the row direction at every single ultrasound transmission, and transmit ultrasound from all of transducers 101a disposed in probe 101.

(5) In the ultrasound diagnostic device according to the embodiment, probe 101 has a configuration in which a plurality of transducers 101a are aligned in the azimuthal direction. However, as probe 101, in addition to a linear probe, a convex probe having a different shape may be used, for example. A convex probe has a larger measurement range of 20 to 30 cm in the depth direction than a linear probe. For this reason, a convex probe is required to reduce the frame rate.

In contrast, in the ultrasound diagnostic device according to a modification, the above-mentioned configuration ensures a sufficient length of the scan line Bxi in the depth direction regardless of the angle of the drawing direction of a scan line with respect to the depth direction and enables measurement of a deep part. As a result, the ultrasound diagnostic device can adapt to the characteristics of the convex probe, that is, a large measurement range in the depth direction.

(6) The shape of a target scan line Bxi is not limited to a liner shape, but may be a rectangular region or a region of another shape, such as a trapezoid, a circular arc, or any other shape. In addition, the number of scan lines Bxi is not limited to a particular number, and may be more than the number in the examples illustrated in the embodiment. In addition, the scan lines Bxi is not limited to being symmetrical with respect to the center line of the transducer row. Alternatively, the target scan line Bxi may be a hourglass-shaped region similar to the ultrasound irradiation region Ax. In addition, the scan lines Bxi set for each transmission event may be set so as to overlap each other in the transducer row direction. The S/N ratio of the generated ultrasound image can be improved by synthesizing the acoustic line signals of the overlapping regions using the synthetic aperture method.

(7) The number of transducers 101a can be set to any number. In addition, the probe may be an electronic scan probe using the linear scanning method. The probe may employ either the electronic scanning method or mechanical scanning method. Alternatively, the probe may employ any one of the linear scanning method, the sector scanning method, and the above-described convex scanning method.

(8) While the present disclosure has been described with reference to the embodiments above, the present invention is not limited to the above embodiments, and the following cases are encompassed within the scope of the present invention.

For example, the present invention may be a computer system having a microprocessor and a memory. The above memory may store programs for the above computer, and the above microprocessor may operate in accordance with the above computer program. For example, the present invention may be a computer system that has a computer program for a diagnostic method of an ultrasound diagnostic device and that operates (or instructs each of connected parts to operate) in accordance with the program.

Furthermore, the following case is encompassed within the scope of the present invention. That is, all or part of the above ultrasound diagnostic device or all or part of the beamforming unit is configured by a computer system including a microprocessor, a storage medium, such as ROM and RAM, and a hard disk unit. The above RAM or hard disk unit stores a computer program that provides an operation the same as that of each of the above units. Each unit provides the function thereof when the above microprocessor operates in accordance with the above computer program.

Some or all of the constituent elements that constitute each of the above-described units may be formed from a single system LSI (Large Scale Integration) chip. A system LSI chip is a super multifunctional LSI chip produced by integrating a plurality of constituent units into one chip. More specifically, the system LSI chip is a computer system including a microprocessor, a ROM, and a RAM. The constituent elements may be individually integrated into a single chip, or some or all of them may be integrated into a single chip. Note that the term "LSI" may be also referred to as "IC", "system LSI", "super LSI" or "ultra LSI", depending on the level of integration. The above RAM has a computer program stored therein, and the computer program provides an operation the same as that of each of the units. The microprocessor operates in accordance with the above computer program and, thus, the system LSI achieves its function. For example, the case where the beamforming method according to the present invention is programed and stored in the LSI chip as a program, and the LSI chip is inserted into a computer to execute the specified program (the beamforming method) is also encompassed within the scope of the present invention.

Note that the circuit integration is not limited to LSI and may be achieved by dedicated circuitry or a general-purpose processor other than LSI. A field programmable gate array (FPGA), which is programmable after fabrication of the LSI chip, or a reconfigurable processor which allows reconfiguration of connections and settings of circuit cells in a LSI chip may be used.

Moreover, should a circuit integration technology replacing LSI appear as a result of advancements in semiconductor technology or other technologies derived from the technology, the functional blocks could be integrated using such a technology.

In addition, some or all of the functions of the ultrasound diagnostic device may be provided by a processor, such as a CPU, executing a program. The present invention may be a non-transitory computer-readable storage medium that stores a program to implement the diagnostic method and the beamforming method for use of the ultrasound diagnostic device described above. The present invention may be practiced by recording a program and a signal in a storage medium and transporting the storage medium so that the program is executed by another independent computer system. It should be noted that the above program can be distributed through transmission media, such as the Internet.

Each of the constituent elements of the ultrasound diagnostic device according to the above embodiment may be achieved by a programmable device, such as a CPU (Central Processing Unit), GPU (Graphics Processing Unit), or processor, and software. The latter configuration is known as GPGPU (General-Purpose computing on Graphics Processing Unit). These constituent elements can be a single circuit component or an aggregate of a plurality of circuit components. In addition, a plurality of constituent elements can be combined to form a single circuit component or an aggregate of a plurality of circuit components.

In the ultrasound diagnostic device according to the above embodiment, the data storage, which is a storage device, is included in the ultrasound diagnostic device. However, the storage device is not limited thereto. The ultrasound diagnostic device may have a configuration in which a semiconductor memory, a hard disk drive, an optical disk drive, a magnetic storage device, and the like is connected thereto externally.

Furthermore, the division into functional blocks described in the block diagrams is only illustrative, and a plurality of the functional blocks may be integrated into one functional block, and a single functional block may be divided into a plurality of functional blocks. In addition, a subset of the functions may be transferred to another functional block. Still furthermore, the functions of a plurality of functional blocks having similar functions may be performed by a single hardware component or software in parallel or in a time-division multiplexing manner.

In addition, the sequence of steps described above is only an example to describe the present invention in detail. The sequence of steps may be a sequence other than the sequence described above. Furthermore, a subset of the steps may be executed simultaneously (in parallel) with other steps.

The ultrasound diagnostic device has a configuration in which a probe and a display unit are connected thereto externally. However, the probe and the display unit may be integrally equipped in the ultrasound diagnostic device.

In addition, the probe may have a subset of the functions of a transceiver unit therein. For example, a transmission electrical signal is generated in the probe on the basis of a control signal for generating the transmission electric signal output from the transceiver unit, and the transmission electrical signal is converted into an ultrasound wave. Furthermore, the received reflected ultrasound wave is converted into a received electrical signal, and a received signal is generated in the probe on the basis of the received electrical signal.

In addition, at least some of the functions of the ultrasound diagnostic devices according to the embodiments and modifications thereof may be combined. Furthermore, all the numbers used above are only examples to describe the present invention in detail, and the present invention is not limited to the numbers used above.

In addition, a variety of modifications of the present embodiment that a person skilled in the art can conceive are encompassed within the scope of the present invention.

Summary

As described above, the ultrasound diagnostic device according to the present embodiment includes a transmitter that causes an ultrasound probe including a plurality of transducers aligned in an azimuth direction to perform a plurality of set transmissions including a plurality of types of ultrasound transmissions for a transmission line which is common, while changing a position of the transmission line in the azimuth direction, a receiver that acquires, from the ultrasound probe, received signals based on reflected waves for the plurality of types of ultrasound transmissions and generates a plurality of types of acoustic line signals, and a hardware processor that generates an imaging signal based on the plurality of types of acoustic line signals. During a time interval between the plurality of types of the ultrasound transmissions in a first set transmission, the transmitter performs at least one of the plurality of types of ultrasound transmissions in a second set transmission that differs from the first set transmission.

According to another aspect, in any one of the above aspects, the set transmission may include, as the plurality of types of ultrasound transmissions, a first ultrasound transmission and a second ultrasound transmission with different drive pulse polarities. The receiver may generate a first acoustic line signal based on a reflected wave related to the first ultrasound transmission and generate a second acoustic line signal based on a reflected wave related to the second ultrasound transmission, and the ultrasound imaging signal generator may generate an imaging signal based on the first acoustic line signal and the second acoustic line signal. During a time interval between the first ultrasound transmission and the second ultrasound transmission in the first set transmission, the transmitter may perform one of the first ultrasound transmission and the second ultrasound transmission in the second set transmission.

According to another aspect, in any one of the above aspects, the transmitter may cause a row of transmit transducers selected from among the plurality of transducer to transmit an ultrasound beam to perform the ultrasound transmission, and a transmission line related to the first set transmission and a transmission line related to the second set transmission may be separated from each other by more than ½ of the length of the row of the transmit transducers in the azimuth direction.

According to another aspect, in any one of the above aspects, an ultrasound diagnostic device may include a transmitter that causes an ultrasound probe including a plurality of transducers aligned in an azimuth direction to perform a plurality of set transmissions each including a plurality of types of ultrasound transmissions for a transmission line which is common, while changing a position of the transmission line in the azimuth direction, a receiver that acquires, from the ultrasound probe, received signals based on reflected waves for the plurality of types of ultrasound transmissions and generates a plurality of types of acoustic line signals, and an ultrasound imaging signal generator that generates an imaging signal based on the plurality of types of acoustic line signals. A time interval between the plurality of types of ultrasound transmissions in the set transmission may be greater than a time interval between two consecutive ultrasound transmissions each included in a different set transmission.

According to another aspect, in any one of the above aspects, the set transmission may include a first ultrasound transmission and a second ultrasound transmission with different drive pulse polarities. The receiver may generate a first acoustic line signal based on a reflected wave related to the first ultrasound transmission and generates a second acoustic line signal based on a reflected wave related to the second ultrasound transmission. The ultrasound imaging signal generator may generate an imaging signal based on the first acoustic line signal and the second acoustic line signal, and a time interval between the plurality of types of ultrasound transmissions in the set transmission may be a time interval between the first ultrasound transmission and the second ultrasound transmission in the set transmission.

According to another aspect, in any one of the above aspects, the time interval between two consecutive ultrasound transmissions each included in a different set transmission may vary frame by frame of the generated imaging signal.

According to another aspect, in any one of the above aspects, an ultrasound diagnostic device may include a transmitter that causes an ultrasound probe including a plurality of transducers aligned in an azimuth direction to perform a plurality of set transmissions each including a plurality of types of ultrasound transmissions for a transmission line which is common, while changing a position of the transmission line in the azimuth direction, a receiver that acquires, from the ultrasound probe, received signals based on reflected waves for the plurality of types of ultrasound transmissions and generates a plurality of types of acoustic line signals, and residual echo detection unit that detects a virtual image signal part of each of a plurality of types of acoustic line signals, a treatment unit that performs treatment on the virtual image signal part of the acoustic line signal having the detected virtual image signal part, and an ultrasound imaging signal generator that generates an imaging signal based on the plurality of types of acoustic line signals including the treated acoustic line signal. A time interval between the plurality of types of ultrasound transmissions in the set transmission may differ from a time interval between two consecutive ultrasound transmissions each included in a different set transmission, and the residual echo detection unit may compare the plurality of types of acoustic line signals with each other and detect a signal part that is not present in another acoustic line signal as the virtual image signal part.

According to another aspect, in any one of the above aspects, the set transmission may include a first ultrasound transmission and a second ultrasound transmission with different drive pulse polarities as the plurality of ultrasound transmissions. The receiver may generate a first acoustic line signal based on a reflected wave related to the first ultrasound transmission and generates a second acoustic line signal based on a reflected wave related to the second ultrasound transmission. The ultrasound imaging signal generator may generate an imaging signal based on the first acoustic line signal and the second acoustic line signal. A time interval between the first ultrasound transmission and the second ultrasound transmission in the set transmission may differ from a time interval between two consecutive ultrasound transmissions each included in a different set transmission, and the residual echo detection unit may compare the first acoustic line signal with the second acoustic line signal and detects, as the virtual image signal part, a signal part of one of the first acoustic line signal and the second acoustic line signal that is not present in the other.

According to another aspect, in any one of the above aspects, the treatment unit may delete an abnormal signal part from each of the first acoustic line signal and the second acoustic line signal.

According to another aspect, in any one of the above aspects, the order in which the first ultrasound transmission and the second ultrasound transmission in the set transmission are performed may be reversed from set transmission to set transmission, and the treatment unit may replace the virtual image signal part of the acoustic line signal line data with a corresponding signal part of acoustic line signal line data of the same polarity in the past than the acoustic line signal line data.

According to another aspect, in any one of the above aspects, the residual echo detection unit may compare the first acoustic line signal with the second acoustic line signal subjected to a time averaging process to detect the virtual image signal part.

According to another aspect, in any one of the above aspects, the time average may be a time average of one or more wavelengths of the lowest frequency in the probe band.

According to another aspect, in any one of the above aspects, the residual echo detection unit may compare the first acoustic line signal with the second acoustic line signal subjected to envelope detection so as to detect the virtual image signal part.

According to another aspect, in any one of the above aspects, the residual echo detection unit may perform a cross-correlation process between the first acoustic line signal and the second acoustic line signal so as to detect, as the virtual image signal part, a part where a significant signal having a low degree of a correlation is present.

According to the embodiment, a method for processing an ultrasound signal includes causing an ultrasound probe including a plurality of transducers aligned in an azimuth direction to perform a plurality of set transmissions including a plurality of types of ultrasound transmissions for a transmission line which is common, while changing a position of the transmission line in the azimuth direction, acquiring, from the ultrasound probe, received signals based on reflected waves for the plurality of types of ultrasound transmissions to generate a plurality of types of acoustic line signals, and generating an imaging signal based on the plurality of types of acoustic line signals. In the transmitting, during a time interval between the plurality of types of the ultrasound transmissions in a first set transmission, at least one of the plurality of types of ultrasound transmissions in a second set transmission that differs from the first set transmission is performed.

According to another aspect, in any one of the above aspects, a method for processing an ultrasound signal may include causing an ultrasound probe including a plurality of transducers aligned in an azimuth direction to perform a plurality of set transmissions each including a plurality of types of ultrasound transmissions for a transmission line which is common, while changing a position of the transmission line in the azimuth direction, generating a plurality of types of acoustic line signals on the basis of reflected waves related to the plurality of types of ultrasound transmissions, and acquiring, from the ultrasound probe, received signals based on the plurality of types of ultrasound transmissions to generate an imaging signal. A time interval between the plurality of types of ultrasound transmissions in the set transmission may be greater than a time interval between two consecutive ultrasound transmissions each included in a different set transmission.

According to another aspect, the ultrasound diagnostic device may further include the ultrasound probe according to any one of the above aspects.

According to another aspect, in any one of the above aspects, a method for processing an ultrasound signal may include causing an ultrasound probe including a plurality of transducers aligned in an azimuth direction to perform a plurality of set transmissions each including a plurality of types of ultrasound transmissions for a transmission line which is common, while changing a position of the transmission line in the azimuth direction, acquiring, from the ultrasound probe, received signals based on reflected waves for the plurality of types of ultrasound transmissions to generate a plurality of types of acoustic line signals, detecting a virtual image signal part of each of a plurality of types of acoustic line signals, performing treatment on the virtual image signal part of the acoustic line signal having the detected virtual image signal part, and generating an imaging signal based on the plurality of types of acoustic line signals including the treated acoustic line signal. A time interval between the plurality of types of ultrasound transmissions in the set transmission may differ from a time interval between two consecutive ultrasound transmissions each included in different set transmission, and in the detecting, the plurality of types of acoustic line signals may be compared with each other so as to detect a signal part that is not present in other acoustic line signals as the virtual image signal part.

According to another aspect, in any of the above aspects, the set transmission may include a first ultrasound transmission and a second ultrasound transmission with different drive pulse polarities as the plurality of ultrasound transmissions. In the generating of the acoustic line signal, a first acoustic line signal may be generated based on a reflected wave related to the first ultrasound transmission, and a second acoustic line signal may be generated based on a reflected wave related to the second ultrasound transmission. In the generating of the imaging signal, an imaging signal may be generated based on the first acoustic line signal and the second acoustic line signal. A time interval between the first ultrasound transmission and the second ultrasound transmission in the set transmission may differ from a time interval between two consecutive ultrasound transmissions each included in a different set transmission.

In the detecting, the first acoustic line signal may be compared with the second acoustic line signal so as to detect, as the virtual image signal part, a signal part of one of the first acoustic line signal and the second acoustic line signal that is not present in the other.

According to another aspect, in any of the above aspects, in the performing of the treatment, an abnormal signal part may be deleted from each of the first acoustic line signal and the second acoustic line signal.

According to another aspect, in any of the above aspects, the order in which the first ultrasound transmission and the second ultrasound transmission in the set transmission are performed may be reversed from set transmission to set transmission, and in the performing of the treatment, the virtual image signal part of the acoustic line signal line data may be replaced with a corresponding signal part of acoustic line signal line data of the same polarity in the past than the acoustic line signal line data.

In addition, according to the present embodiment, a program that causes a computer to perform an ultrasound signal process is provided. The ultrasound signal process includes causing an ultrasound probe including a plurality of transducers aligned in an azimuth direction to perform a plurality of set transmissions including a plurality of types of ultrasound transmissions for a transmission line which is common, while changing a position of the transmission line in the azimuth direction, acquiring, from the ultrasound probe, received signals based on reflected waves for the plurality of types of ultrasound transmissions to generate a plurality of types of acoustic line signals, and generating an imaging signal based on the plurality of types of acoustic line signals. In the transmitting, during a time interval between the plurality of types of the ultrasound transmissions in a first set transmission, at least one of the plurality of types of ultrasound transmissions in a second set transmission that differs from the first set transmission is performed.

Supplement

Each of the embodiments described above is a preferred example of the present invention. A value, a shape, a material, a constituent element, the positions and the connection form of the constituent elements, steps, and the sequence of steps described in the embodiments are only examples and shall not be construed as limiting the scope of the present invention. In addition, among the constituent elements in the embodiments, the constituent element that does not appear in an independent claim, which has the broadest scope, is described as an optional constituent element that constitutes a more preferred form.

The order in which the above-described processes are performed is for illustrative purposes to describe the present invention in detail and may be in any order other than the above-described order. In addition, a subset of the above processes may be performed simultaneously (in parallel) with other processes.

In addition, for ease of understanding the invention, the scale of the components of each figure listed in the above embodiments may differ from the actual one. Furthermore, the present invention is not limited by the description of the above embodiments and can be changed as necessary without departing from the scope of the present invention.

INDUSTRIAL APPLICABILITY

The ultrasound diagnostic device and the program according to the present disclosure are useful for improving the performance of existing ultrasound diagnostic devices, especially for improving the quality of images. In addition, the present disclosure can be applied not only to an ultrasound diagnostic device but also to other applications, such as sensors using multiple array elements.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound diagnostic device, comprising:
a transmitter connected to an ultrasound probe that includes a plurality of transducers aligned in an azimuth direction, the transmitter being configured to cause the plurality of transducers of the ultrasound probe to perform a plurality of set transmissions while changing a position of the transmission line in the azimuth direction of the ultrasound probe, each set transmission of the plurality of set transmissions consisting of a first ultrasound transmission and a second ultrasound transmission with different drive pulse polarities for a respective transmission line;
a receiver configured to acquire, from the ultrasound probe, received signals based on reflected waves for the first ultrasound transmission and the second ultrasound transmission and generate a first acoustic line signal based on a reflected wave related to the first ultrasound transmission and generate a second acoustic line signal based on a reflected wave related to the second ultrasound transmission; and
a hardware processor configured to generate an imaging signal based on the first acoustic line signal and the second acoustic line signal; and
a first memory, a second memory, and a third memory,
wherein during a time interval between the first ultrasound transmission and the second ultrasound transmission in a first set transmission of the plurality of set transmissions, the transmitter is configured to perform the first ultrasound transmission or the second ultrasound transmission in a second set transmission of the plurality of set transmissions that differs from the first set transmission of the plurality of set transmissions and the receiver generates a further acoustic line signal from the first ultrasound transmission or the second ultrasound transmission in the second set transmission of the plurality of set transmissions;
wherein the first acoustic line signal, the second acoustic line signal, and the further acoustic line signal being stored in the first memory, the second memory, and the third memory in accordance with a transmission order,
wherein the transmitter is configured to cause a row of transmit transducers selected from among the plurality of transducer to transmit an ultrasound beam to perform the ultrasound transmission, and
wherein a transmission line related to the first set transmission and a transmission line related to the second set transmission are separated from each other by more than ½ of the length of the row of the transmit transducers in the azimuth direction.

2. The ultrasound diagnostic device according to claim 1, wherein transmission lines 1-n are arranged in order in the azimuth direction and are divided into lower number transmission lines 1 to (½)n and upper number transmission lines (½)n+1 to n, and the first set transmission of the plurality of set transmissions is for one of the lower number transmission lines and the second set transmission of the plurality of set transmissions is for one of the upper number transmission lines.

3. The ultrasound diagnostic device according to claim 1, wherein the time interval between the first ultrasound transmission and the second ultrasound transmission in the each set transmission of the plurality of set transmissions prevents a reflected wave of the first ultrasound transmission from a deep reflected tissue from reaching the ultrasound probe during a reception period of the second ultrasound transmission.

4. An ultrasound diagnostic device, comprising:
a transmitter connected to an ultrasound probe that includes a plurality of transducers aligned in an azimuth direction, the transmitter being configured to cause the ultrasound probe to perform a plurality of set transmissions while changing a position of the transmission line in the azimuth direction, each set transmission of the plurality of set transmissions consisting of a first ultrasound transmission and a second ultrasound transmission with different drive pulse polarities for a respective transmission line, and the first ultrasound transmission and the second ultrasound transmission for the each set transmission of the plurality of set transmissions being performed before a successive one of the plurality of set transmissions is performed;
a receiver configured to acquire, from the ultrasound probe, received signals based on reflected waves for the first ultrasound transmission and the second ultrasound transmission and generate a plurality of types of acoustic line signals; and a hardware processor configured to generate an imaging signal based on the plurality of types of acoustic line signals, wherein a time interval between the first ultrasound transmission and the second ultrasound transmission in the each set transmission of the plurality of set transmissions is greater than a time interval between two consecutive ultrasound transmissions each included in different set transmissions of the plurality of set transmissions.

5. The ultrasound diagnostic device according to claim 4, wherein the time interval between the two consecutive ultrasound transmissions each included in different set transmissions of the plurality of set transmissions varies frame by frame of the generated imaging signal.

6. The ultrasound diagnostic device according to claim 4, wherein the time interval between the first ultrasound transmission and the second ultrasound transmission in the each set transmission of the plurality of set transmissions prevents a reflected wave of the first ultrasound transmission from a deep reflected tissue from reaching the ultrasound probe during a reception period of the second ultrasound transmission.

7. An ultrasound diagnostic device, comprising:
a transmitter connected to an ultrasound probe that includes a plurality of transducers aligned in an azimuth direction, the transmitter being configured to cause the plurality of transducers of the ultrasound probe to perform a plurality of set transmissions while changing a position of the transmission line in the azimuth direction of the ultrasound probe, wherein each set transmission of the plurality of set transmissions includes a pair of ultrasound transmissions of different polarity for a respective transmission line and wherein the pair of ultrasound transmissions for the each set transmission of the plurality of set transmissions are performed before a successive one of the plurality of set transmissions is performed;
a receiver configured to acquire, from the ultrasound probe, received signals based on reflected waves for the pair of ultrasound transmissions and generate a plurality of types of acoustic line signals including a first acoustic line signal and a second acoustic line signal; and
a hardware processor configured to detect a virtual image signal part of each of a plurality of types of acoustic line signals, perform treatment on the virtual image signal part of the acoustic line signal having the detected virtual image signal part by deleting the virtual image signal part or replacing the virtual image signal part by a corresponding signal part of a previous acoustic line signal line data of a same polarity, and generate an imaging signal based on the plurality of types of acoustic line signals including the treated acoustic line signal,
wherein a time interval between the pair of ultrasound transmissions in the each set transmission of the plurality of set transmissions differs from a time interval between two consecutive ultrasound transmissions each included in different set transmissions of the plurality of set transmissions, and
wherein the hardware processor is configured to perform cross-correlation processing of the first acoustic line signal and the second acoustic line signal and detects a signal part that is not present in another acoustic line signal as the virtual image signal part.

8. The ultrasound diagnostic device according to claim 7, wherein the each set transmission of the plurality of set transmissions includes a first ultrasound transmission and a second ultrasound transmission with different drive pulse polarities as the pair of ultrasound transmissions,
wherein the receiver is configured to generate the first acoustic line signal based on a reflected wave related to the first ultrasound transmission and generate the second acoustic line signal based on a reflected wave related to the second ultrasound transmission,
wherein the hardware processor is configured to generate an imaging signal based on the first acoustic line signal and the second acoustic line signal,
wherein a time interval between the first ultrasound transmission and the second ultrasound transmission in the each set transmission of the plurality of set transmissions differs from a time interval between two consecutive ultrasound transmissions each included in a different set transmission of the plurality of set transmissions, and
wherein the hardware processor is configured to compare the first acoustic line signal with the second acoustic line signal and detects, as the virtual image signal part, a signal part of one of the first acoustic line signal and the second acoustic line signal that is not present in the other.

9. The ultrasound diagnostic device according to claim 8, wherein the hardware processor is configured to delete an abnormal signal part from each of the first acoustic line signal and the second acoustic line signal.

10. The ultrasound diagnostic device according to claim 8, wherein an order in which the first ultrasound transmission and the second ultrasound transmission in the each set transmission of the plurality of set transmissions are performed is reversed from set transmission to set transmission, and
wherein the hardware processor is configured to replace the virtual image signal part with the corresponding signal part of the previous acoustic line signal line data of the same polarity.

11. The ultrasound diagnostic device according to claim 8, wherein the hardware processor is configured to compare the first acoustic line signal with the second acoustic line signal subjected to a time averaging process to detect the virtual image signal part.

12. The ultrasound diagnostic device according to claim 11, wherein the time average is a time average of one or more wavelengths of the lowest frequency in the probe band.

13. The ultrasound diagnostic device according to claim 8, wherein the hardware processor is configured to compare the first acoustic line signal with the second acoustic line signal subjected to envelope detection so as to detect the virtual image signal part.

14. The ultrasound diagnostic device according to claim 8, wherein the hardware processor is configured to detect, as the virtual image signal part, a part where a signal with a significant signal having a low degree of a correlation is present.

15. A non-transitory computer readable storage medium storing therein a computer readable program causing a computer to perform ultrasound signal processing comprising:
causing an ultrasound probe including a plurality of transducers aligned in an azimuth direction to perform a plurality of set transmissions while changing a position of the transmission line in the azimuth direction, each set transmission of the plurality of set transmissions consisting of a first ultrasound transmission and a second ultrasound transmission with different drive pulse polarities for a respective transmission line;

acquiring, from the ultrasound probe, received signals based on reflected waves for the first ultrasound transmission and the second ultrasound transmission to generate a first acoustic line signal based on a reflected wave related to the first ultrasound transmission and generate a second acoustic line signal based on a reflected wave related to the second ultrasound transmission; and generating an imaging signal based on the first acoustic line signal and the second acoustic line signal, wherein in the transmitting, during a time interval between the first ultrasound transmission and the second ultrasound transmission in a first set transmission of the plurality of set transmissions, a first ultrasound transmission or a second ultrasound transmission in a second set transmission of the plurality of set transmissions that differs from the first set transmission of the plurality of set transmissions is performed and a further acoustic line signal is generated from the first ultrasound transmission or the second ultrasound transmission in the second set transmission, wherein the first acoustic line signal, the second acoustic line signal, and the further acoustic line signal are stored in the first memory, the second memory, and the third memory in accordance with a transmission order, wherein the computer causes a row of transmit transducers selected from among the plurality of transducers to transmit an ultrasound beam to perform the ultrasound transmission, and wherein a transmission line related to the first set transmission and a transmission line related to the second set transmission are separated from each other by more than ½ of the length of the row of the transmit transducers in the azimuth direction.

* * * * *